United States Patent
De Campo et al.

(10) Patent No.: US 12,083,255 B2
(45) Date of Patent: Sep. 10, 2024

(54) PHOTOCATALYTIC SANITIZING REACTOR

(71) Applicant: Inpigest S.r.l., Vergiate (IT)

(72) Inventors: Michele De Campo, Vergiate (IT); Giuseppe Bavestrello, Loano (IT)

(73) Assignees: Earth & Sea Group S.r.l., Loano (IT); Inpigest S.r.l., Vergiate (IT)

(*) Notice: Subject to any disclaimer, the term of this patent is extended or adjusted under 35 U.S.C. 154(b) by 1002 days.

(21) Appl. No.: 17/414,373

(22) PCT Filed: Sep. 28, 2018

(86) PCT No.: PCT/IB2018/057566
§ 371 (c)(1),
(2) Date: Jun. 16, 2021

(87) PCT Pub. No.: WO2019/064264
PCT Pub. Date: Apr. 4, 2019

(65) Prior Publication Data
US 2022/0040357 A1 Feb. 10, 2022

(30) Foreign Application Priority Data

Sep. 29, 2017 (IT) .................. 102017000109448

(51) Int. Cl.
*A61L 9/18* (2006.01)
*A61L 2/08* (2006.01)
*B01J 19/12* (2006.01)
*B01J 19/24* (2006.01)
*B01J 23/30* (2006.01)
(Continued)

(52) U.S. Cl.
CPC ............ *A61L 9/18* (2013.01); *A61L 2/088* (2013.01); *B01J 19/127* (2013.01); *B01J 19/2415* (2013.01); *B01J 23/30* (2013.01); *B01J 35/39* (2024.01); *F24F 8/167* (2021.01); *A61L 2202/11* (2013.01); *A61L 2202/16* (2013.01); *A61L 2209/12* (2013.01); *A61L 2209/15* (2013.01); *B01J 2219/2453* (2013.01); *B01J 2219/2498* (2013.01)

(58) Field of Classification Search
None
See application file for complete search history.

(56) References Cited

U.S. PATENT DOCUMENTS

| | | |
|---|---|---|
| 5,069,885 A | 12/1991 | Ritchie |
| 5,516,492 A * | 5/1996 | Dong ............... C02F 1/325 422/186 |
| 5,933,702 A | 8/1999 | Goswami |

(Continued)

FOREIGN PATENT DOCUMENTS

| | | |
|---|---|---|
| EP | 0306301 | 3/1989 |
| WO | 2008113128 | 9/2008 |

(Continued)

*Primary Examiner* — Jelitza M Perez
(74) *Attorney, Agent, or Firm* — Themis Law

(57) ABSTRACT

A sanitizing photocatalytic reactor suitable for air liquid or liquid fluids includes a reaction region containing a photocatalyst selected from nanotechnological materials of natural light photocatalyst type, which is supported on an inert support or mixed with a plastic material, and an illumination region having white color LED lights, the reaction region further having one or more channels through which the fluids to be sanitized flow.

19 Claims, 16 Drawing Sheets

(51) Int. Cl.
 *B01J 35/39* (2024.01)
 *F24F 8/167* (2021.01)

(56) References Cited

U.S. PATENT DOCUMENTS

2011/0142725 A1   6/2011  Liu
2011/0171080 A1*  7/2011  Lo ........................... B01J 35/39
                                                422/186.3

FOREIGN PATENT DOCUMENTS

| WO | 2009026568 | 2/2009 | | |
|----|------------|--------|----|----|
| WO | WO-2009026568 A1 * | 2/2009 | ............ | B01J 19/006 |
| WO | 2011070206 | 6/2011 | | |

* cited by examiner

FIG.5
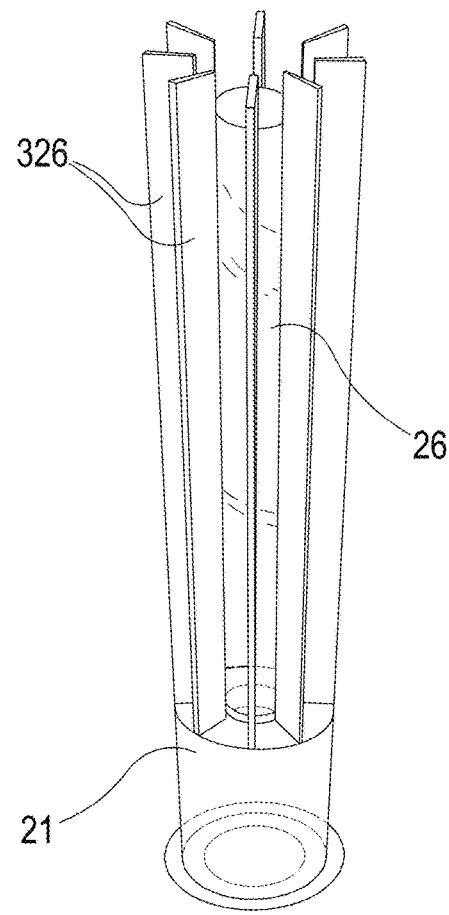
FIG.6

PHOTOCATALYTIC SANITIZING REACTOR

The present invention relates to a sanitizing photocatalytic reactor suitable for air liquid or liquid fluids.

Photocatalysis is a catalytic process that can be used in different applications such as the abatement of pollutants and bacteria from liquid and gaseous streams, the purification of water and air, the synthesis of chemical compounds of interest and the conversion of the solar energy into chemical energy.

A typical photocatalyst is a semiconductor that, by absorbing one photon having higher energy than the gap, between valence band and conduction band, modifies the structure of its molecular orbitals with electrons, defined photoelectrons, of the valence band passing to the conduction band, with the formation of positive photo-gaps in the same valence band.

These charge carriers have short life: they can, by means of different mechanisms, recombine and return to the original configuration of the semiconductor i.e. generate a flow of surface current, because of the potential gradient that was created at the band level. The lowest energy level of the conduction band defines the reduction potential of the photoelectrons whereas the higher energy level of the valence band determines the oxidizing power of the photo-gaps, respectively.

When the reagents diffuse on the catalyst surface, they are chemisorbed on an active site and can participate to redox reactions. The absorbed species can be photo-reduced if its reduction standard potential is higher than that of the photoelectrons. Otherwise the photo-gaps can cause the oxidation, if their potential is higher than that of the subject molecules.

The reaction mechanisms are not yet exactly known: it is believed that the molecules are directly oxidized or reduced or else they react, in an adsorbed phase or in solution, by means of very reactive radical intermediates. These radicals are the result of the interaction effect of the charge photo-carriers with, for example, oxygen and water, contained in a solution.

The photocatalytic effectiveness depends on different parameters: the number and stability over time of the charge carriers that have been photo-generated, the absorption/desorption balance and the type of reaction considered.

The photocatalyst is a semiconductor photocatalyst material, such as for example $WO_3$, that can be activated with white light basically with an emission temperature in the range from 5500° K to 6500° K, that can intervene in the redox processes thanks to its particular electronic structure. The applications are multiple: degradation of atmospheric pollutants (nitrogen oxides, volatile organic molecules), antimicrobial action, coating of building materials with self-cleaning, anti-fogging properties, and properties of degradation of pollutants in water.

Currently novel photocatalytic reactors are being studied and designed that allow sanitizing liquid and gaseous streams and in particular purifying water and air by means of the abatement of pollutants and bacteria.

We have made novel, relatively simple photocatalytic reactors that allow achieving significant abatements both of pollutants and bacteria to be used directly or to be mounted on suction systems.

It is an object of the invention a sanitizing photocatalytic reactor suitable for gaseous or liquid fluids essentially comprising a reaction region containing a photocatalyst selected from the materials known as photocatalysts activated with sunlight, which photocatalyst is distributed on a support made of inert material or else is mixed with a matrix made of plastic material, and an illumination source oriented so to emit light radiation beams incident on said photocatalyst, i.e. on said support and which illumination source is constituted by one or more white color LED lights, where said reaction region comprises one or more channels through which said fluids to be sanitized flow, said channels being delimited and/or containing said supports for the photocatalyst.

According to an embodiment said supports are constituted by the surfaces of supporting elements lapped by a gas or liquid flow to be treated, said supporting elements being constituted by low transmissivity material for the light radiation incident on the photocatalyst.

Still according to an embodiment, in combination with one or more of the previous features, the photocatalyst is deposited on the surface or surfaces exposed to light radiation activating the same and/or impregnated in the matrix of the material said supports are made of, in the form of particles having nanometric size, i.e. in the particle size range between 1 and 100 nm.

Still according to a further feature that can be provided in combination with one or more of any feature of the aforementioned embodiments, the invention advantageously provide that the supporting elements for the photocatalyst constitute a constructive unit independent of the constructive elements constituting the light source or sources and the hardware/software units supplying power to the same, said two constructive units being provided with mutual fixing removable elements.

As it will be seen later, in particular in the field of the fluid treatment, this feature allows obviating the need to have specialized personnel who knows both the technology of the fluid supply circuits and the technology related to the illumination systems with electric power supply. Thus, in particular, for what concerns the water treatment for domestic use both for food and disposal, it is possible to leave the installation of the hydraulic circuit to the person specialized in these circuits and intervene later with the assembly of the light sources by using an electrician or lighting technician.

As photocatalyst different substances are known, such as for example $TiO_2$, $ZnO$, $Fe_2O_3$, $CdS$, $CdSe$, $WO_3$, $MoO_3$, $V_2O_5$, $SnO_2$.

The photocatalyst preferably used in the state of the art is $TiO_2$. This preferably requires the use of ultraviolet radiation for activating it. However, by subjecting this material to doping with Fe, Cr, Co, Mo, V, B, C, N, S and F, it is possible to modify the same and make it activable also by use of light with a wavelength in the spectral region of the visible light radiation.

A first problem for spreading these devices and the related treatment methods consists in being able to increase efficiency both from the point of view of the effect of purification and sanitizing, and from the point of view of energy efficiency and flow rate of the treated fluid. Maximizing these parameters constitutes a trade-off condition among them as an increase of the flow rate through the reactor requires an increase of the reaction efficiency and usually an increase in radiation energy for the activation of the photocatalyst.

Despite all the examples of implementation of these photocatalytic reactors use $TiO_2$, it has surprisingly been found that the efficiency, in terms of the effect of the sanitizing treatment, is significantly higher using $WO_3$ as a photocatalyst.

As it will appear from the following description, the best results were obtained by combining the photocatalyst made of, or comprising, $WO_3$ with an activating light radiation having an intensity of at least 300 Lux and a wavelength in the visible light.

According to a preferred embodiment, said light radiation has an intensity of at least 300 Lux and a white color with a gradation from 5300° K to 10000° K.

Preferably, LED type lamps are suitable as light sources.

In combination with the aforementioned features, the parameter optimization is also achieved thanks to a constructive configuration of the supports for the photocatalyst and lamps or light sources emitting the radiation activating the same, in combination with the elements for conveying the flows of gaseous and/or liquid fluid to be treated.

As already highlighted earlier, it is a feature to separate one from the other, in operating units that can be mounted independently and can be aggregated, the interface part with the fluid flow of the reactor and the generation part of the activating radiation.

A further feature that can be provided in any combination or sub-combination with the aforementioned ones, provides that the light radiation is emitted with a propagation direction incident on the surfaces of the supporting elements of the photocatalyst and with an opening angle ranging from 100 to 120°.

Despite the configuration that will be described below can be used with any type of fluid to be treated, being it gaseous or liquid, some of the embodiments described will have a preferential use with gaseous fluids and others will have with liquid fluids.

In a preferred embodiment the sanitizing photocatalytic reactor, preferably suitable for gaseous fluids, comprises:

a reaction region containing several sheets of an inert support, which are placed parallel to one another and equally spaced at a minimum distance from one another of 7.5 mm, or multiples of the same, thus forming several substantially uniform channels, said sheets being covered by a layer of photocatalyst material that can be activated by solar light radiation and/or by a light radiation according to one or more of the aforementioned features;

a supporting region of an illumination source with LED lights emitting a white color light radiation with an opening and a propagation direction incident against the walls of said sheets so as to illuminate them, said illumination source being constituted by at least one LED lamp for each channel laterally delimited by two adjacent sheets and said LED lamps being distributed along the illumination source in such a position that it coincides with a corresponding channel.

Thanks to the aforementioned configuration, the surfaces of the sheets of each channel that has been formed between one and the other sheet of two adjacent sheets is illuminated by at least one LED lamp, said sheets being arranged side by side with each other and said LED lamps being arranged on one or more strips along an axis perpendicular to the longitudinal axes of the channels and/or sheets delimiting the same.

According to an embodiment, said LED strips can be supported by one or more walls of a container within which the power supply of said LED lights is placed, itself also having an elongated shape and placed perpendicularly to the axes of the channels and/or sheets delimiting the channels.

According to an embodiment variation said set of container housing the power supply and LED lamps strips can also be possibly supported by one or more or by all of said sheets.

According to an embodiment, the inert material of the supporting elements for the photocatalyst, i.e. the material the sheets are made of, on whose surface the photo-catalyst is applied, is made of iron or zinc-coated steel or mixtures of appropriate and suitably treated plastic materials.

Still according to a feature, the size of the sheets is defined depending on the size of the application to be implemented both for what concerns length and height (the total surface).

Advantageously, the preferred thickness is comprised in a range from 0.5 mm to 1 mm, preferably from 0.7 mm to 0.8 mm instead.

In an embodiment, the distance between the sheets can also be a multiple of the minimum distance of about 7.5 mm.

The choice and the sizing have the principle of dividing portions of fluid in a determined number of parallel channels thus obtaining a uniform distribution of the fluid input and output, so much that it can be completely treated in the most effective system possible, ensuring at the same time the correct illumination of all the surfaces in contact.

For the sizing it is important to verify the flow rate of the fluid (gaseous or liquid) to be sanitized for determining the length size (depending on the air direction) of the sheets that cannot be undersized with respect to the ratio between reaction time and throughput.

Furthermore, in the reactor other sheets can be provided still parallel to each other but in series with respect to the previous ones.

According to an embodiment the reactor can comprise at least one first layer of sheets parallel to each other and oriented with their sides in the direction of the fluid flow and at least one further second layer of sheets parallel to each other and oriented with their sides in the direction of the fluid flow, the sheets of the first layer being oriented with their longitudinal axes in a non-parallel direction, preferably perpendicular to the direction of the longitudinal axes of the sheets provided in the second layer of sheets, and for the first layer of sheets and the second layer of sheets a dedicated illumination source being provided and comprising at least one line or strip of LED lamps, which is oriented in a direction perpendicular to the longitudinal axes of the sheets of the layer of sheets said illumination source is combined with, for the activation of the photocatalyst.

So it is formed a grid constituted by two orders of sheets placed side by side and crossed with each order of sheets its illumination source.

Thus, the flow to be treated is not separated in adjacent slices, but in a matrix of trickles according to the two dimensions that underlie the light of passage or the flow section.

A reactor according to one or more of the preceding features can be part of machines or equipment conveying fluid flows in particular gaseous flows, such as for example conditioners or aerators, or other similar devices.

In a second preferred embodiment, the sanitizing photocatalytic reactor is particularly suitable for the sanitizing treatment of liquid fluids and is constituted by a tubular element, preferably having a cylindrical shape, constituting a tube segment through which the liquid fluid is passing and inside which the supporting elements for the photocatalyst are provided, whereas the light source or sources can alternately or in combination be provided internally or externally to said tubular element, the latter being made transparent in case the light source or sources are arranged externally to the same.

A first embodiment comprises two coaxial tubes of different diameters arranged one inside the other so as to form a channel through which the fluid flow is passing, which has annular section and delimited by the tube having smaller diameter and by that having larger diameter, the tube having larger diameter being made of inert material partially or completely covered on the inner surface by a catalyst layer according to one or more of the variations described above and, the tube having smaller diameter being made of plastic material or glass transparent to the light radiation activating the photocatalyst and the tube having smaller diameter houses in its inside at least one strip of LED lamps generating the activating radiation.

Still according to a further feature, the inner tube can have sheets made of inert material supporting the photocatalyst on the outside.

The LED lamps are arranged on at least one or more strips placed longitudinal along the mantle surface of the tube near, or on the inner or outer surface of said tube having smaller diameter.

The number of strips of longitudinal LED lamps is preferably 2 to 4 and they are distributed angularly equidistant to each other along the mantle surface of the tube having smaller diameter.

In a third preferred embodiment the sanitizing photocatalytic reactor suitable for liquid fluids is in the form of filtering unit provided in its inside with sanitizing elements depicted so far, accompanied by the necessary illumination.

According to an embodiment the filtering unit comprises a tubular container inside which a cylindrical filtering cartridge is provided, the latter comprising mantle walls constituted by a grid, the inner surface of said grid is possibly covered by synthetic fabric with micro-holes (60 microns), said grid and said fabric constituting supporting surfaces for the photocatalyst, whereas inside the cylindrical filtering cartridge a supporting element for the photocatalyst is housed that is coaxial to said cylindrical filter, one end of the cylindrical filter being closed and the other end being linked to a fluid inlet union, whereas the tubular container is closed at one end and is open at the opposite end and linked to an outlet union, whereas one or more illumination lamps are provided, which are constituted by a set of LED lamps that radiate an activating light radiation on the surfaces provided with the photocatalyst of the filtering cartridge, the support for the photocatalyst provided inside the same and the fabric layer which covers internally said grid.

In this embodiment the fluid is fed to the container and is forced to go beyond the fabric with micro-holes, whereas the cartridge will contact the reactor made of inert and/or plastic material.

A preferred embodiment provides that both the device in the form of tubular segment and the filtering unit described above respectively have the wall of the tubular segment having larger diameter and the container of the filtering unit that is made of transparent material, i.e. material having transmissivity features of the light radiation activating the photocatalyst, whereas the illumination source or sources are provided outside the mantle wall of said tubular segment or said container and are oriented so as to emit a beam of light radiation towards the inside of said tubular segment or said container, the power supply unit of said light source or sources also being provided outside said tube segment or said container.

According to a further embodiment the light source or sources combined to the tube segment or container are in the form of elements that can be fixed separately from said tube segment or said container.

Various embodiments are possible: a first variation provides that the light sources are constituted by annular supporting elements of a plurality of LED lamps provided on the radially inner side of the said annular elements, one or more of said annular elements being able to be fixed in predetermined axial positions according to predetermined distributions along the axial extent of the tube segment or container.

An embodiment variation provides that the LED lamps are mounted in a line on a flexible, ribbon-like support that can be helically wound around the mantle surface of the tubular segment or container.

Still according to an embodiment variation, one or more strips of adjacent LED lamps is mounted on a band made of flexible material, which band can be wound around the mantle surface of the tubular segment or container, the strips of LED lamps being oriented parallel to the winding axis, i.e. the axis of the tubular segment or container.

Still according to an embodiment, the inner wall of said band is made of reflective material for the activating radiation emitted by the LED lamps.

Still according to a feature, the outer tubular segment has, at the terminal ends, connection fittings sealing to further parts of the feeding pipe of the fluid, such as for example clamping flanges, terminals coupled by screwing or the like.

An embodiment variation for the treatment of the fluid according to the present invention provides, inside the transparent tube segment and/or cylindrical filtering cartridge of the filtering unit, a support made of inert material for the photocatalytic material, which support is constituted by a plurality of sheets arranged with their longitudinal axes parallel to each other and crossing each other at the median longitudinal axes, whereas the light sources have at least one LED or at least one line of LEDs placed coincident with the corner region delimited by two adjacent sheets.

According to a preferred embodiment, a device for sanitizing fluids comprises in a more general form thereof, a tubular pipe segment made of transparent material, whose ends are provided with connection fittings sealing to further elements of a feeding circuit of said fluid, a supporting element for the photocatalyst being housed inside said tubular segment, which element has at least one surface facing the mantle wall of the tubular segment and on which surface the photocatalyst is provided, said surface being in contact with the fluid flow in said tubular segment, and one or more light sources arranged outside the mantle wall of the tubular segment and orientated with one or more LED lamps in the direction of the central axis of the tubular segment i.e. in the direction of the supporting element of the photocatalyst, i.e. the surface of the same on which said photocatalyst is provided, one or more power supply units of said light source or sources, said light sources being mounted on supports that can be coupled in a fixable and separable way to the mantle wall of the tube segment.

Regarding the filtering unit according to the present invention, a preferred embodiment provides a cup-shaped container closed at one end and whose opposite end is linked to a connection pipe, the mantle wall of the container being transparent i.e. having a predetermined transmissibility to the light radiation activating a photocatalyst;

a tubular cylindrical filtering cartridge having a mantle surface constituted by a grid or a permeable filtering membrane, which cylindrical cartridge is housed in the container and is closed at the end corresponding to that of the container and is open at the opposite end that is linked to a connecting union, the fluid flow passing inside the filtering cartridge and from this in the container through the mantle wall of said filtering cartridge and exiting the union linked to said container, whereas inside the filtering cartridge a supporting element of the photocatalyst material is housed, said supporting element, i.e. the surfaces on which the photocatalyst is provided being in contact with the fluid flow and one or more light sources arranged outside the mantle wall of said container being provided and oriented with one or more LED lamps in the direction of the central axis of said container, i.e. in the direction of the supporting element of the photocatalyst, i.e. the surface of the same on which said photocatalyst is provided, one or more power supply units of said light source or sources, said light sources being mounted on supports couplable in a fixable and separable way to the mantle wall of said container.

According to an embodiment variation, the photocatalyst can also be provided on the mantle surfaces of the filtering cartridge.

Advantageously said illumination source or sources are made according to one or more embodiment variations described above.

Similarly, alternatively or in combination with one or more embodiment variations of said light sources also the supporting element of the photocatalytic material can be made according to one or more of the features described above.

In particular, it is advantageous that the illumination sources are constituted by one or more strips of adjacent LED lamps, each of which is mounted at a distance from those adjacent on the wall of a band made of flexible material, which band can be wound around the mantle surface of the tubular segment, the strips of LED lamps being oriented parallel to the winding axis, i.e. the axis of the tubular segment or container.

Similarly the supporting element for the photocatalyst material is advantageously constituted by a plurality of sheets arranged with their longitudinal axes parallel to each other and crossing each other at the median longitudinal axes, whereas the light sources have at least one LED or at least one line of LEDs placed coincident with the corner region delimited by two adjacent sheets.

Still according to an embodiment variation that can be provided in combination with the device for the sanitizing treatment particularly intended for fluid flows or with the liquid filtering unit, the tubular segment and/or the container can have different lengths that are equal to a predetermined multiple of a minimum length, the supporting element finned for the photocatalytic material and the filtering cartridge respectively being constituted by at least one module or by an axial combination of said modules constituted respectively by an axial segment of supporting element and said cylindrical filtering cartridge having a length corresponding to the said minimum length of the tubular segment or container, said modules being able to be fixed to each other in axially aligned position to each other.

In combination with this modular construction, also the light source or sources comprise a module having a minimum axial length on which the lines of LED lamps having a corresponding minimum axial length are distributed, said minimum axial length being commensurate with the axial length of the modules of supporting element and modules of cylindrical filtering cartridge.

The deposit of a primer can possibly be provided on the surfaces treated with a photocatalyst.

The illumination systems with white color LED light that can be used in the photocatalytic reactors in accordance with the invention can be selected and placed so as to ensure the illumination minimum limit of at least 300 Lux.

The parameters of said LED light illumination systems are preferably the following:
Power Supply: 12 to 24 Vcc
Power Consumption: 12 to 14 W mt
Color temperature: 5300 to 10000 K
Light flow: 1100 to 1600 Lm/mt
Beam Angle: 100° to 120°
Turn-on time: <0.3 sec The reaction generated by switching the illumination on is that typical of the photocatalysis, thus strong oxidation that, by attacking the molecules lapping the photocatalytic reactor, decomposes them into carbon dioxide and water vapor in a very small amount.

The photocatalytic reactor, as it has been designed and made, has the ability to be extended and used in multiple form by simply extending in size and thus in surface, enlarging and/or elongating the cartridge or by using several sections of the same.

In its various forms the catalytic reactor can be mounted in machines or equipment that aspirates fluids and after passing them inside the reactor, where the sanitizing from pathogens in addition to fungi and molds takes place, they give them back to the surrounding environment. This system is called recirculation system as the passage of the fluid in the machine or equipment and thus in the reactor occurs several times, as a ratio to the cubage of the room and the flow rate of the ventilation inside the machine or equipment.

Once the photocatalytic reactor has been placed inside air pipes bringing the fluid from outside the rooms pushed by UTA (air treatment unit) and without opposing mechanical resistance to the fluid in transit, the reactor acts with its own principle, sanitizing from the pollutants that are present during the passage.

The same principle is in the use of the reactor inside input and output water pipes that, simply by pressure, cross the reactor and undergo the sanitizing treatment.

The features of the invention and the advantages deriving from it will be more evident from the following description of embodiments depicted in the attached drawings, wherein.

Figure 2:
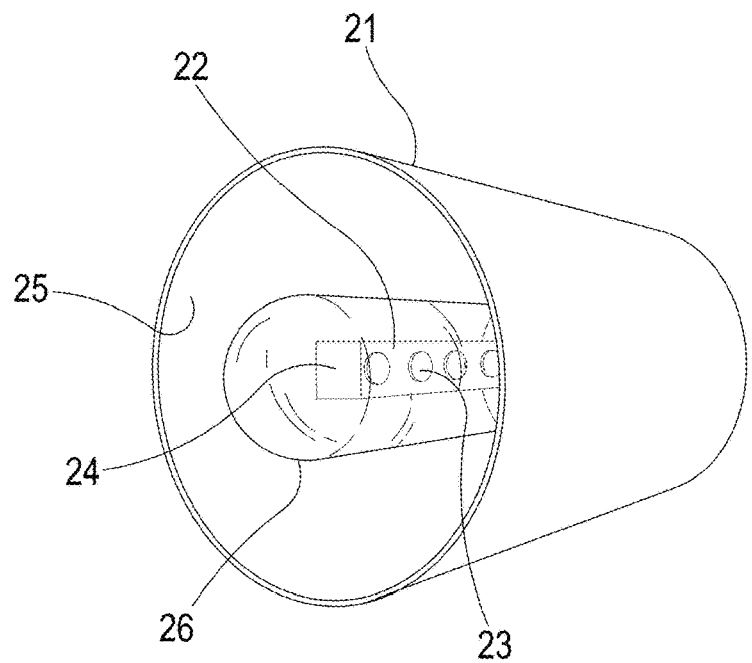
FIG. 2 (a, b) illustrates a second embodiment of the sanitizing photocatalytic reactor.
Figure 2:
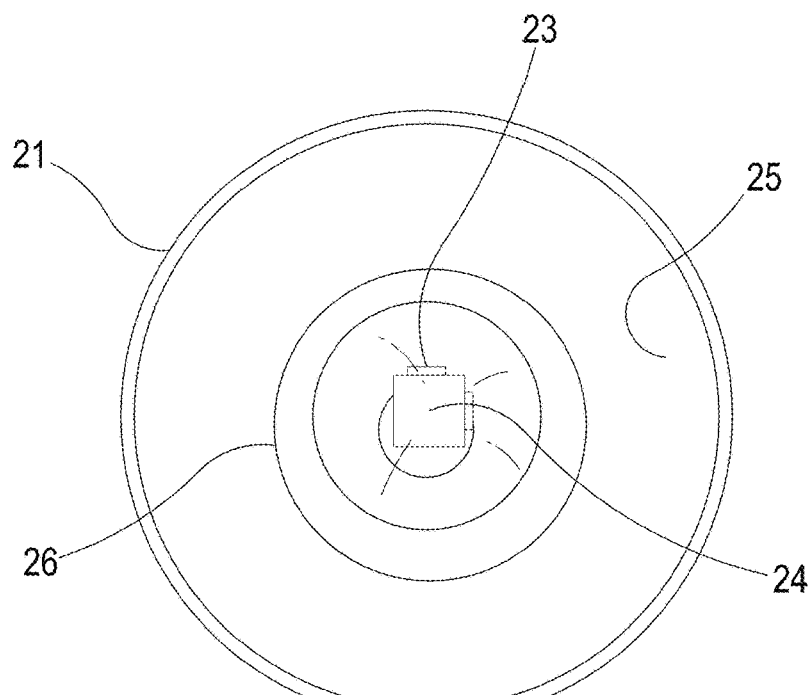

Figures from 3 to 6 show different embodiment variations of the embodiment according to FIG. 2;

In FIGS. 7 to 12 different constructive variations of a third embodiment are showed, wherein the photocatalytic reactor is built inside a common water filter.

Figure 13:
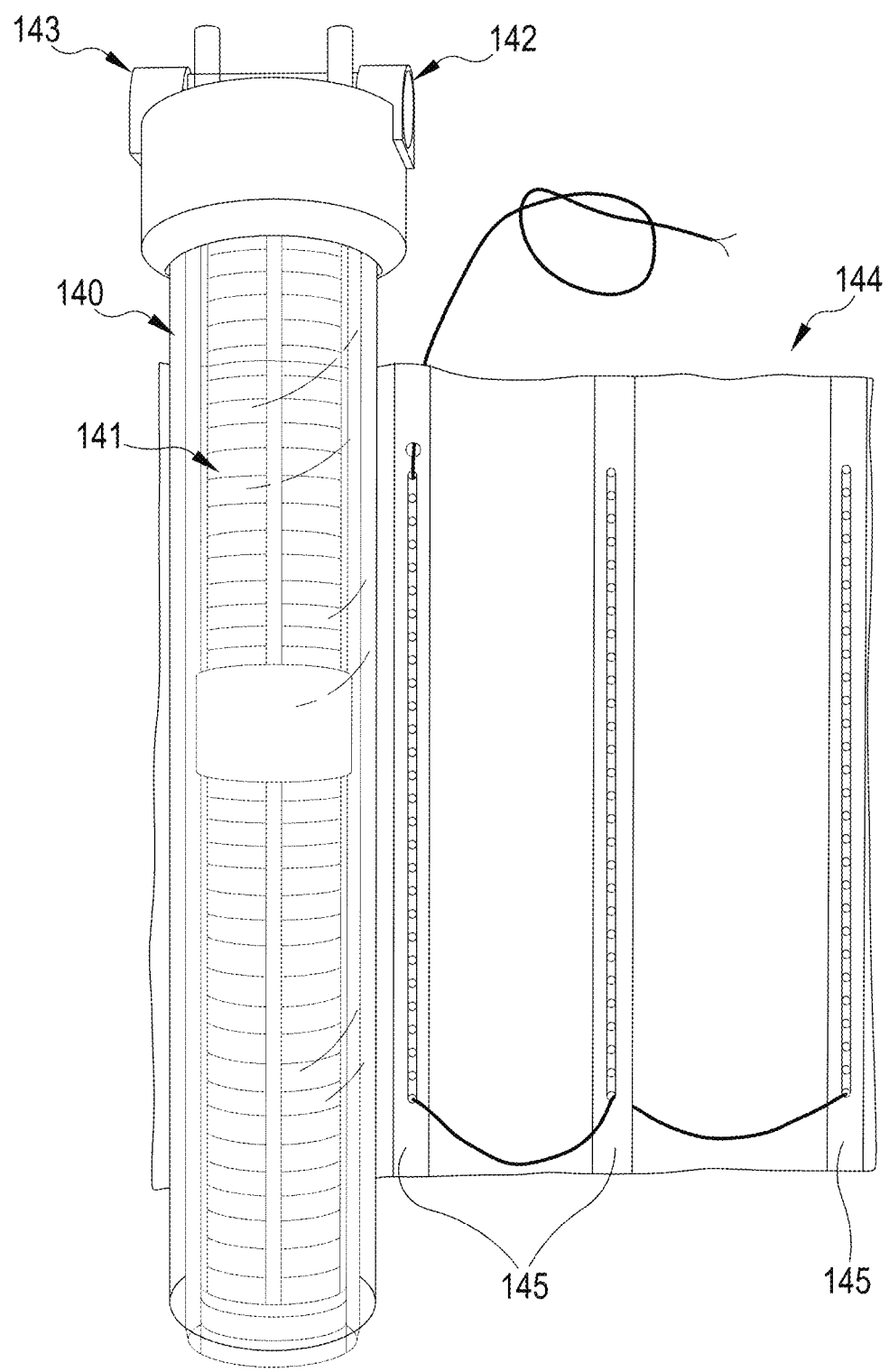

FIG. 13 shows a preferred embodiment variation of a filtering unit of fluids according to the present invention.

Figure 14:
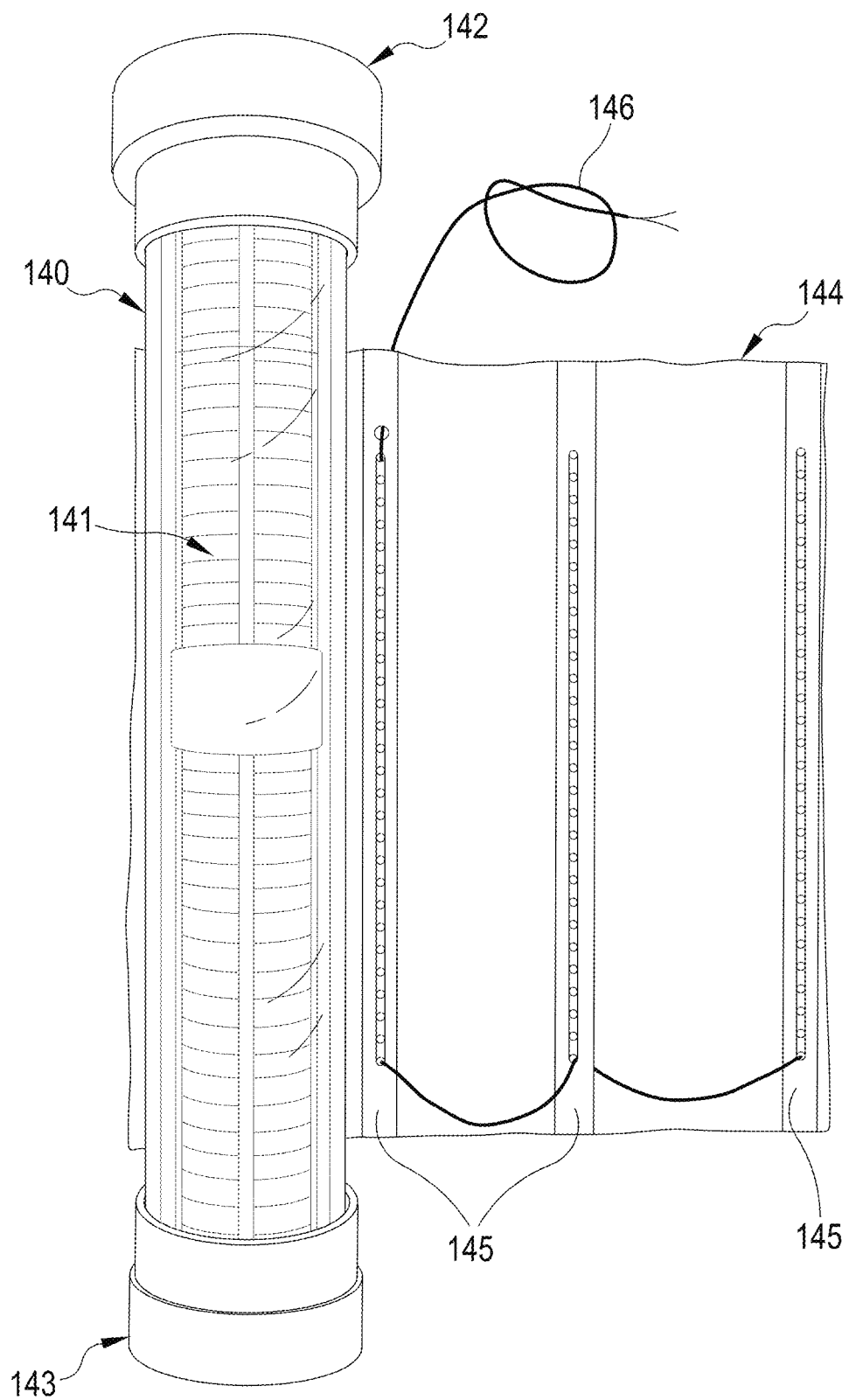

FIG. 14 shows a preferred embodiment of the present invention for the treatment of flows of passing liquid fluids.

Figure 15:
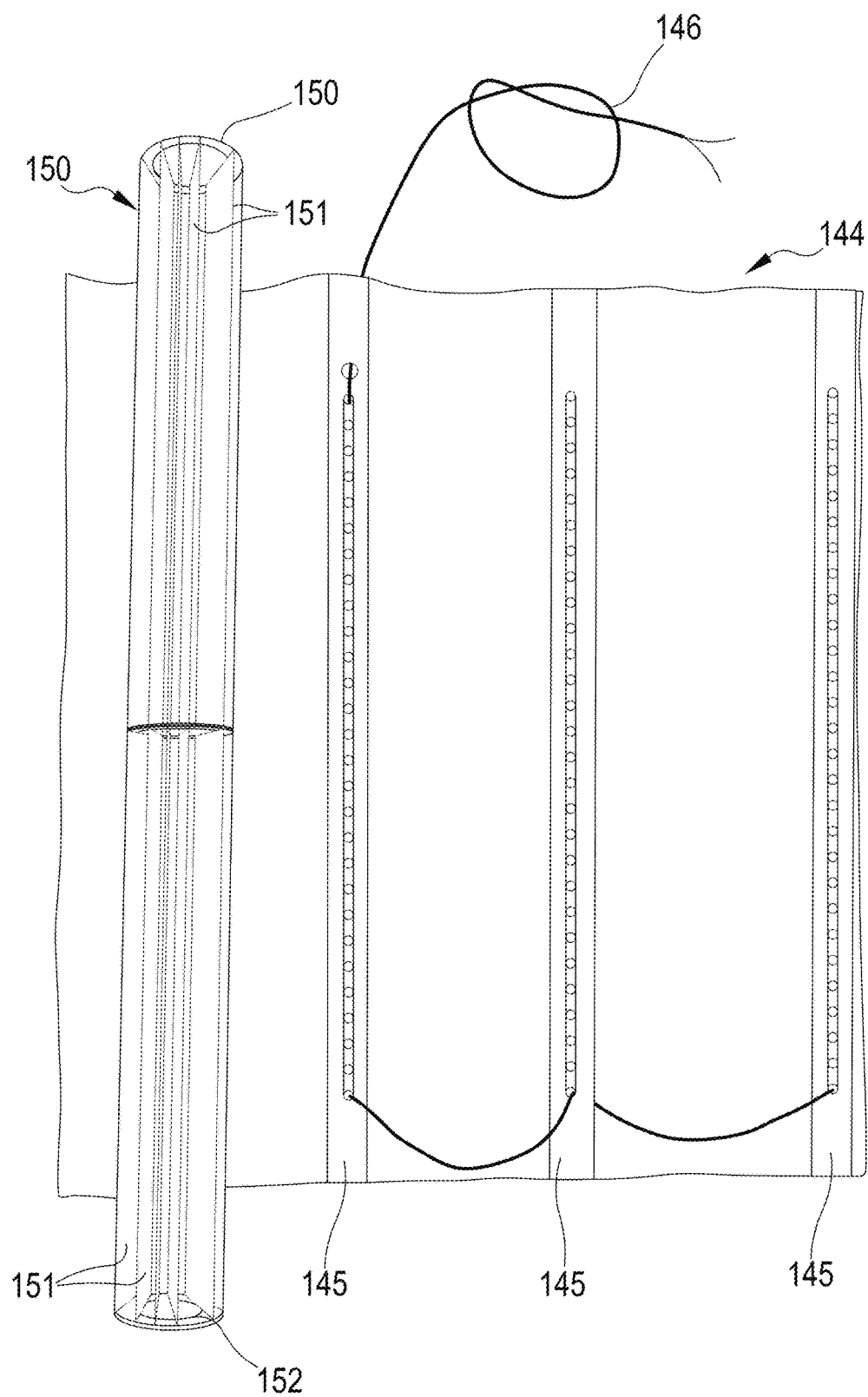

FIG. 15 shows the supporting element of the photocatalytic material and the band for fixing the sources of the activating light radiation provided for the embodiments of FIGS. 13 to 14.

Figure 16:
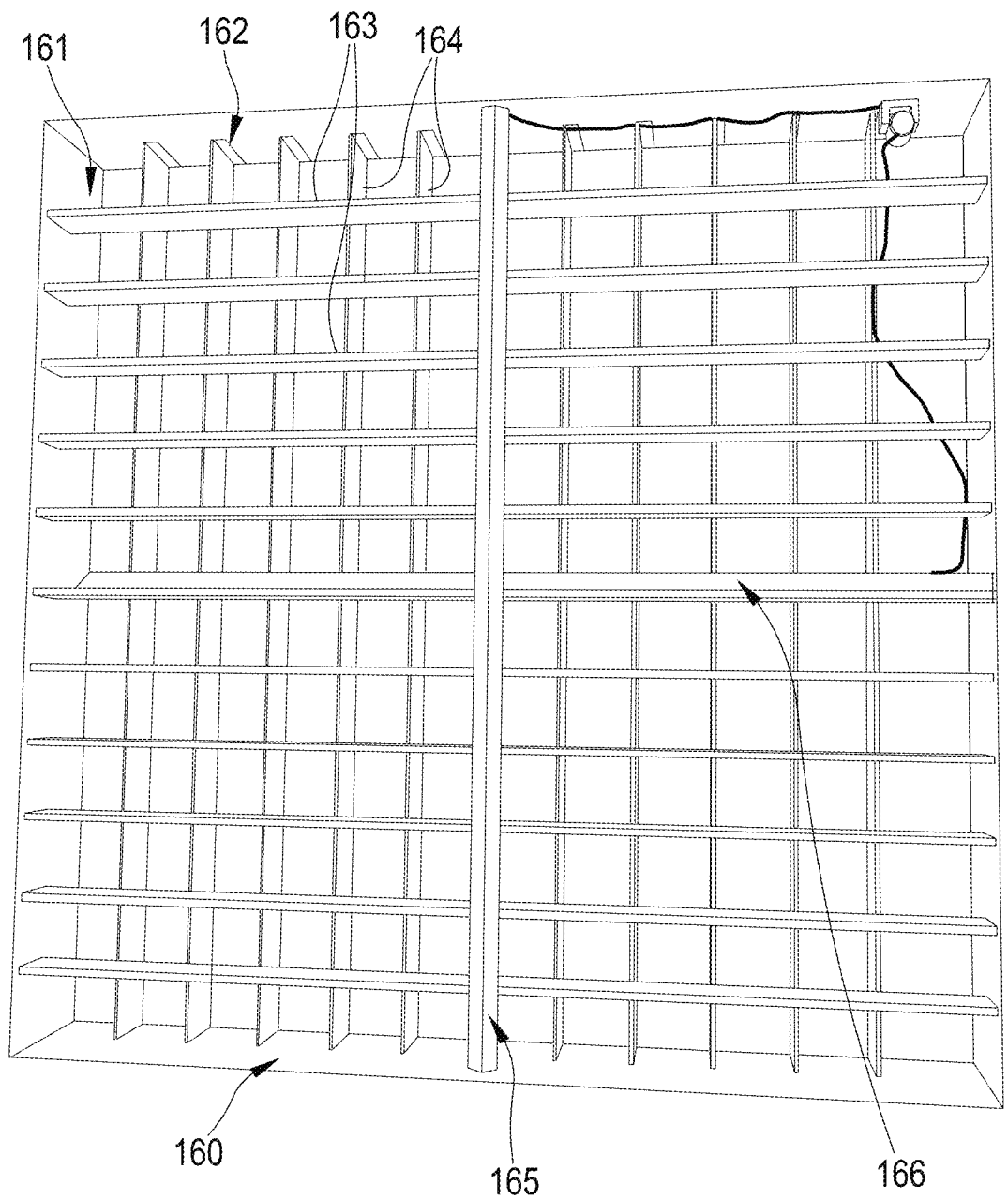

FIG. 16 shows an embodiment variation of a treatment module according to the present invention particularly suitable for the treatment of gaseous fluids and wherein the supports for the photocatalytic material are constituted by two arrays of sheets adjacent to each other and crossed as a grid.

Figure 17:
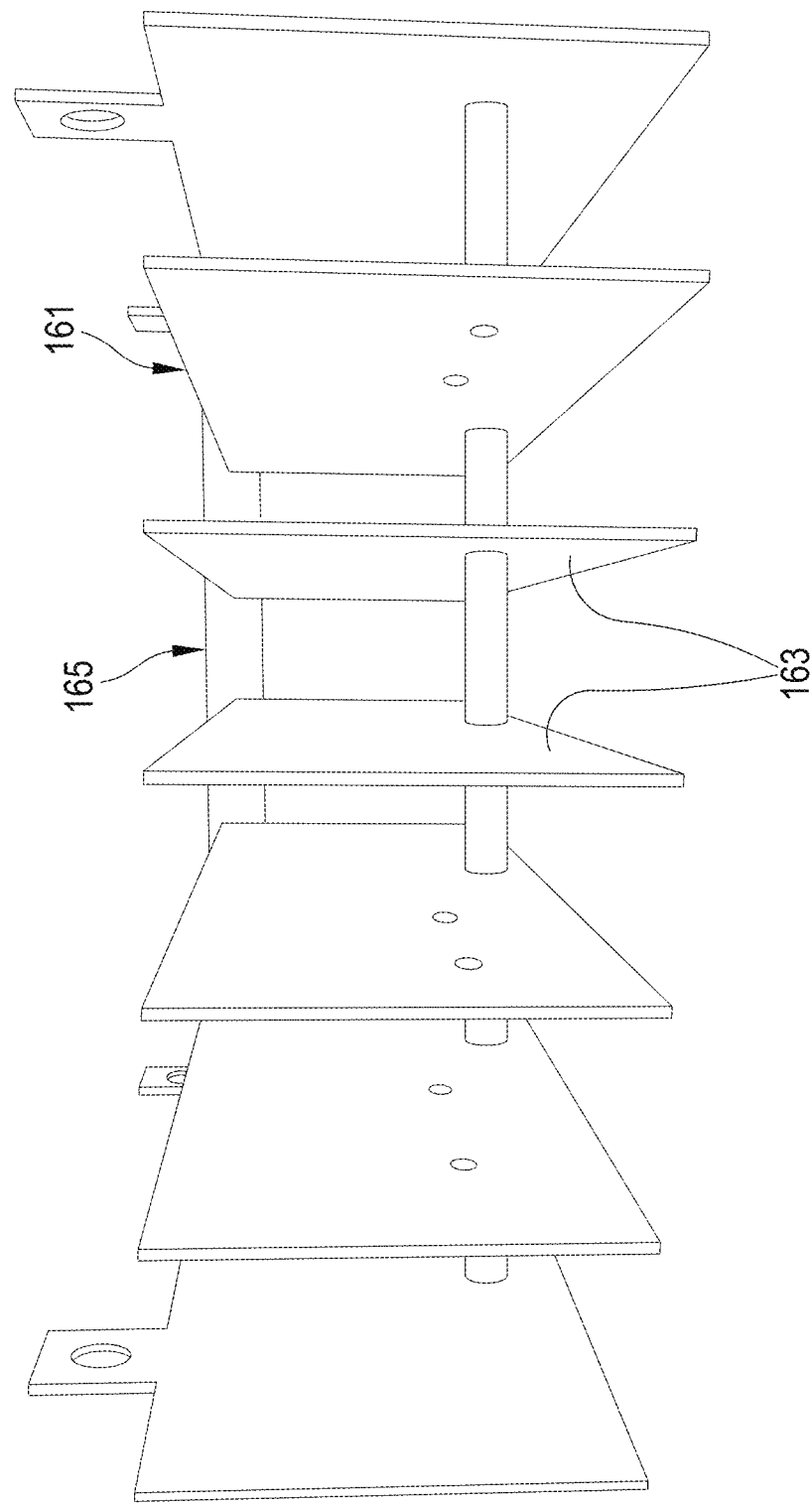

FIG. 17 shows a further embodiment variation for the treatment of gaseous fluids.

Figure 18:
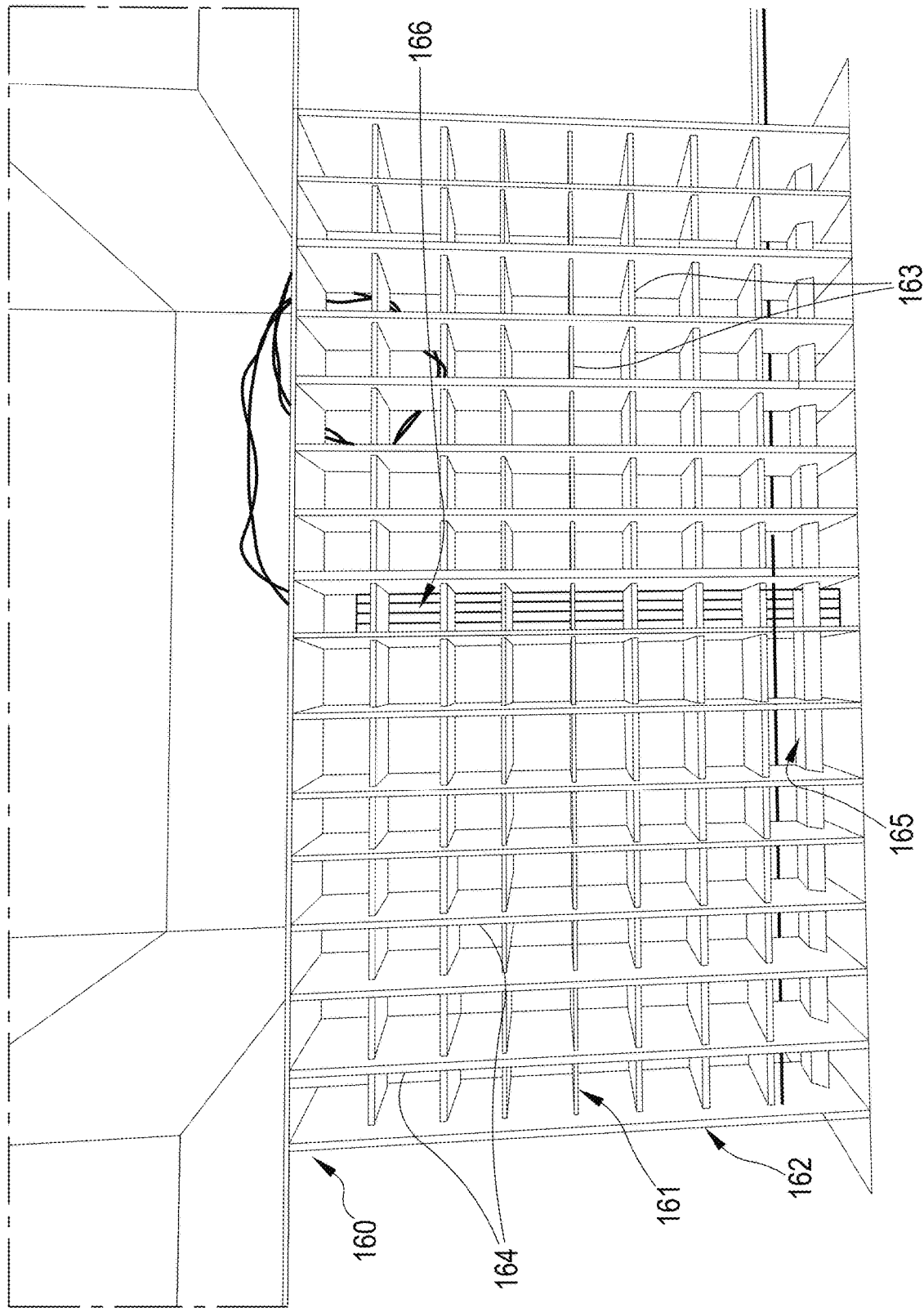

FIG. 18 shows a further embodiment variation for the treatment of gaseous fluids.

Figure 19:
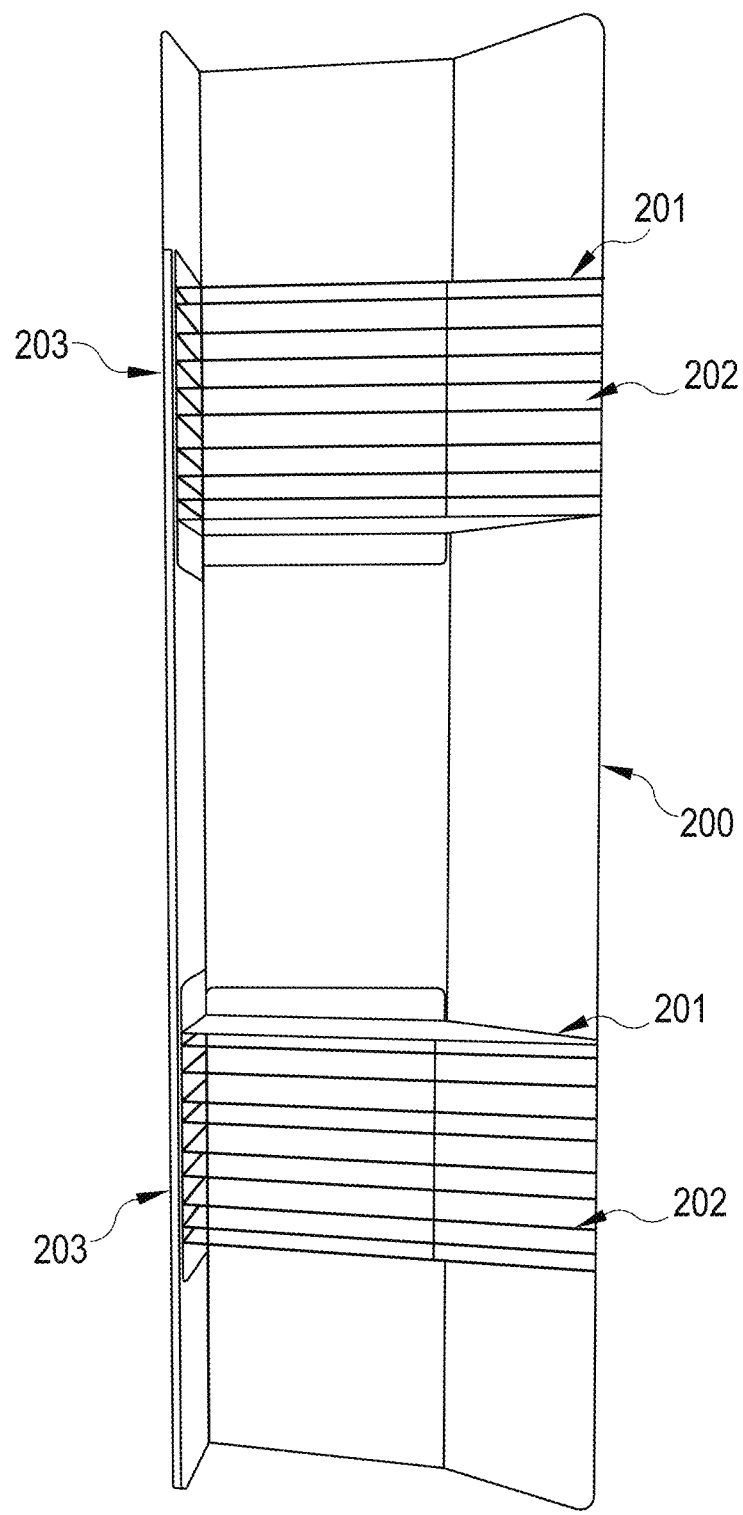
Figure 20:
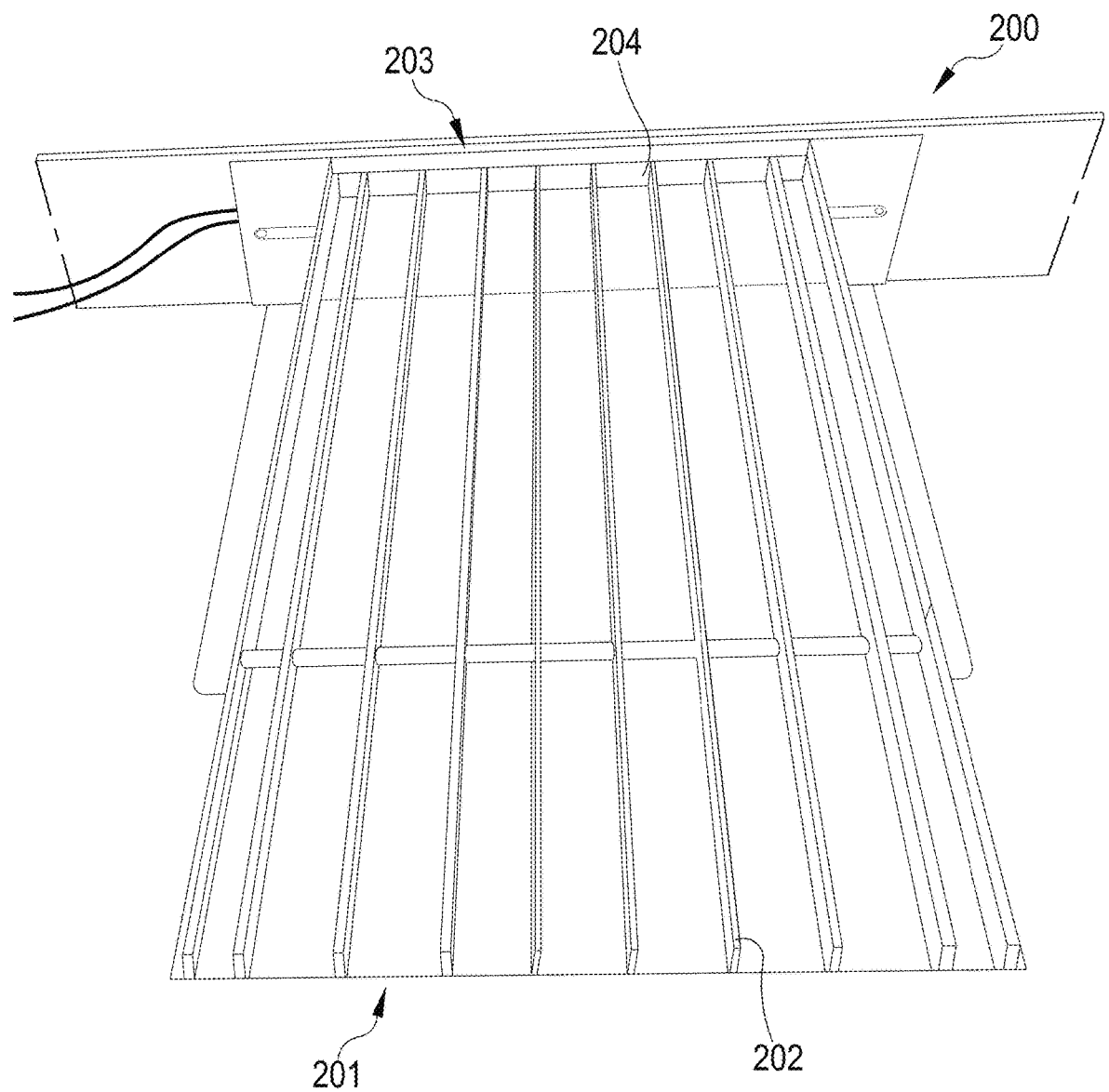

FIGS. 19 and 20 show a device for the treatment of gaseous fluids according to the present invention intended to be mounted in a console of an air conditioning device or the like.

Figure 21:
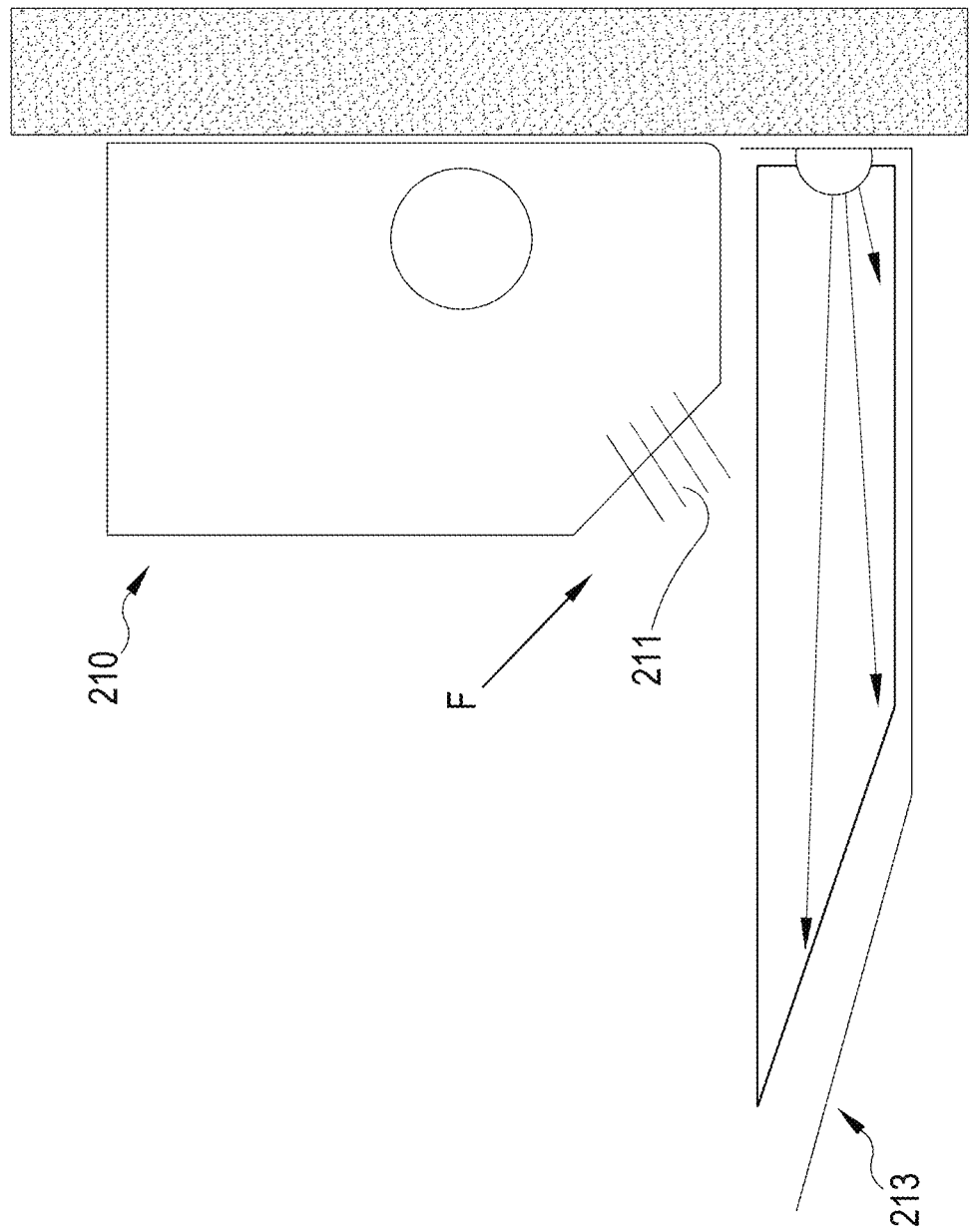

FIG. 21 schematically shows the combination of the sanitizing device according to FIGS. 19 and 20 and a console of a conditioning device.

Figure 1:
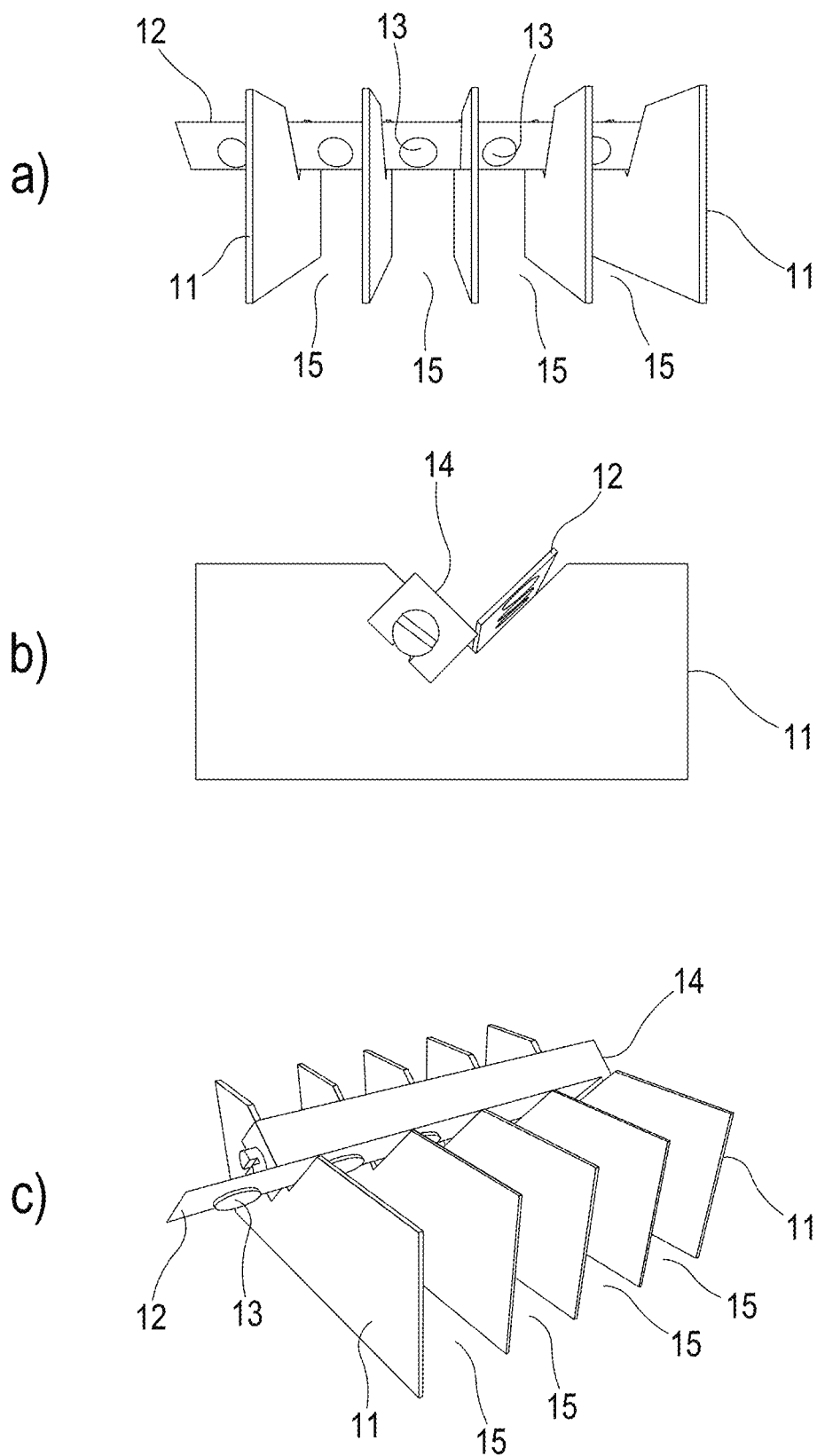
FIG. 1 (a, b, c) illustrates a first embodiment of the sanitizing photocatalytic reactor.

In FIG. 1 (a: side view; b: front view; c: perspective view) is showed one version of the first embodiment of the sanitizing photocatalytic reactor according to the invention, specifically designed for air liquid fluids. The photocatalytic reactor comprises sheets 11 parallel and equally spaced from one another, made of inert material covered by the photocatalyst, and a strip 12 of white color LED lights 13, perpendicular to the parallel axes of the sheets, placed in contact with said parallel sheets.

The fluid passes through the channels 15 that are formed between the parallel sheets 11, uniformly dividing and sanitizing itself.

In FIG. 2 a second embodiment of the sanitizing photocatalytic reactor according to the invention is shown, specifically designed for liquid fluids. The tubular photocatalytic reactor comprises a double tubular concentric tube: a tube having larger diameter 21 covered on its inner surface of the photocatalyst and a tube having smaller diameter 26 and the strips 22 of LED lights (23). In this case the channel wherein the fluid to be sanitized passes is only one 25.

FIGS. 3 to 6 show different embodiment variations of the embodiment according to FIG. 2 and in these figures for identical parts identical numbers are used.

Figure 3:
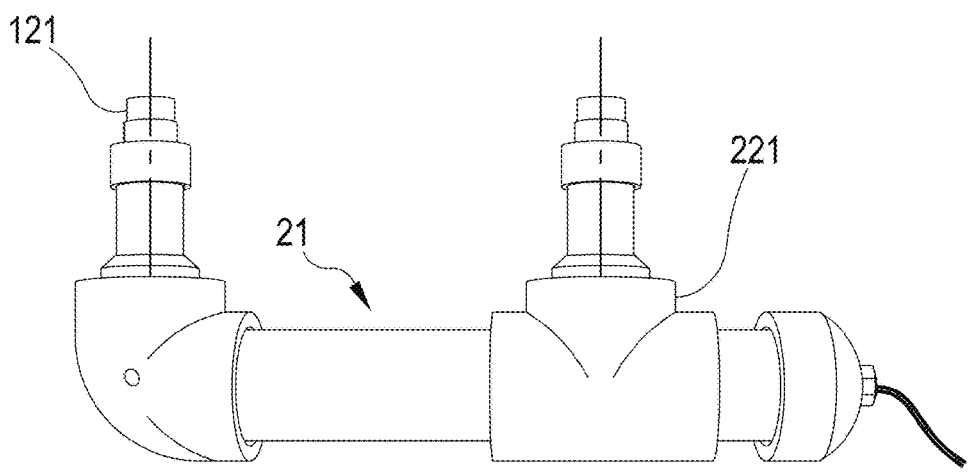
Figure 4:
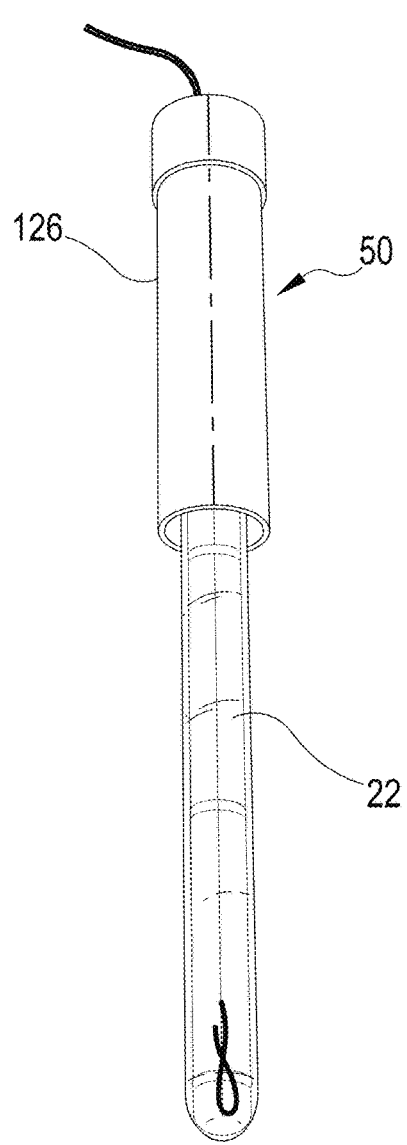

FIG. 3 shows a reactor according to FIG. 2 wherein a section of external containment tube having larger diameter 21 has an inlet and an outlet 121, 221 for the fluid that are provided on branches transversal to the tube axis 21, for example a terminal curve and a T-joint. The T-joint has a section coaxial to the tube 21 through whose opening the glass tube 26 containing one or more strips of LED lamps 22 can be inserted. The tube 26 made of glass or other transparent material is sealingly connected with a terminal 126 remaining outside the T-joint and having the coupling fittings sealing to the T-joint and the power supply wire of the LEDs. Possibly the terminal 126 can also contain the electronic circuit supplying power to, and controlling the LEDs. Such a construction is depicted in the embodiment of FIG. 4 in which it is in the form of LED candle 50.

FIGS. 5 and 6 show further variations of constructive parts of the reactor according to FIG. 2.

In FIG. 5, the inner tube 26 has a crown of radial sheets 326 along its outer walls, which confers to the former a star-shaped cross section and divides the passage between the outer tube 21 and the inner tube 26 in longitudinal channels having section like a sector of annular chamber having angular extent lower than 360° for each channel. Also the sheets 326 can be treated, i.e. covered by photocatalyst and the tube 26 is transparent and constitutes for example the wall of the candle 50 that will have a star-shaped section or else a chamber housing the transparent part of the candle 50.

FIG. 6 shows the outer tube 21 treated with the photocatalyst according to a further embodiment.

Figure 7:
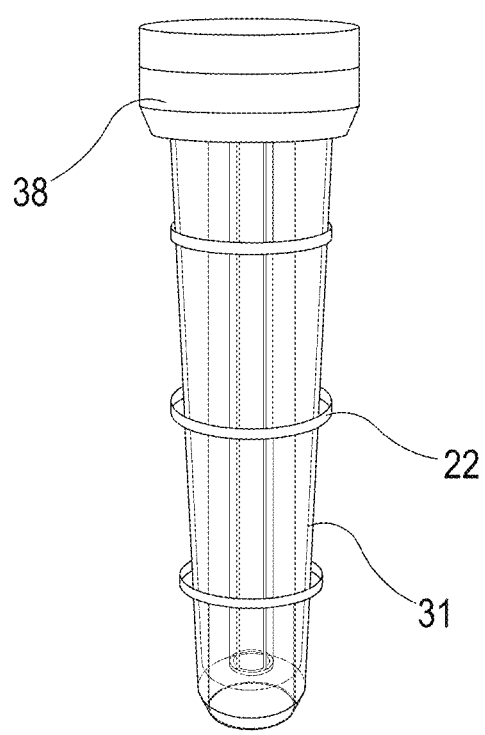
Figure 8:
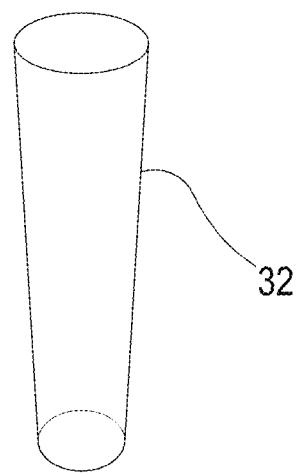
Figure 9:
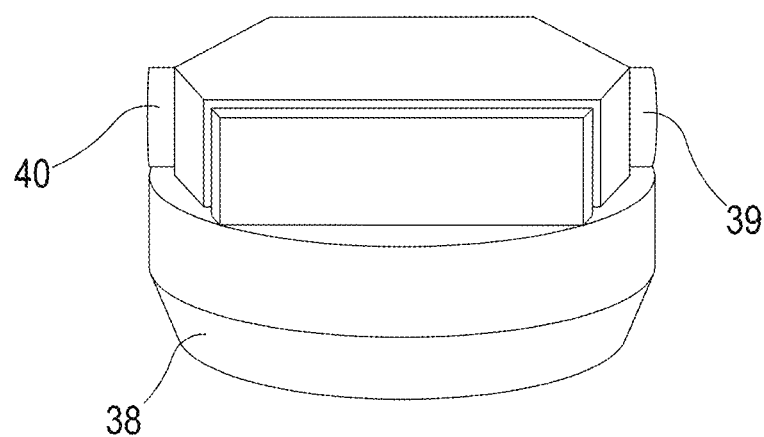
Figure 10:
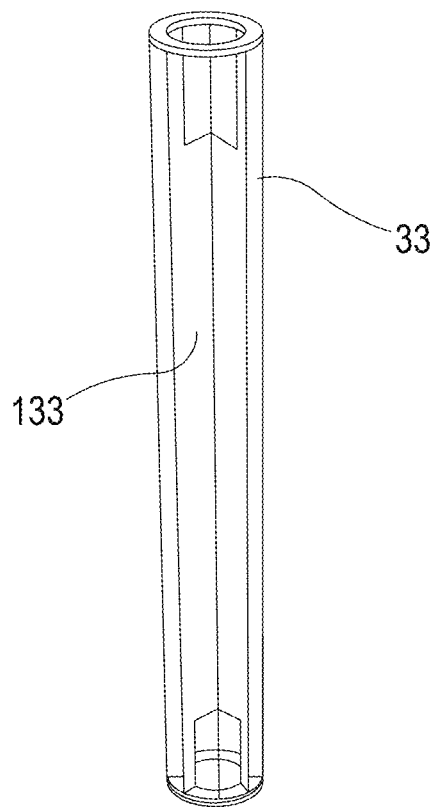
Figure 11:
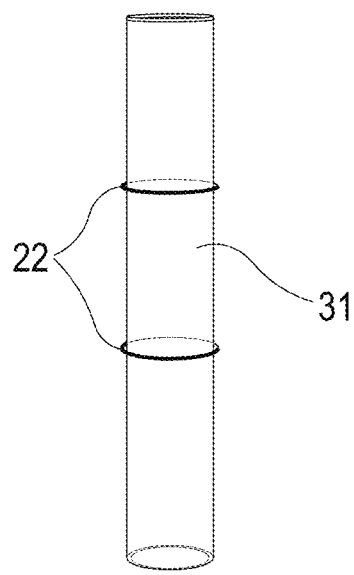
Figure 12:
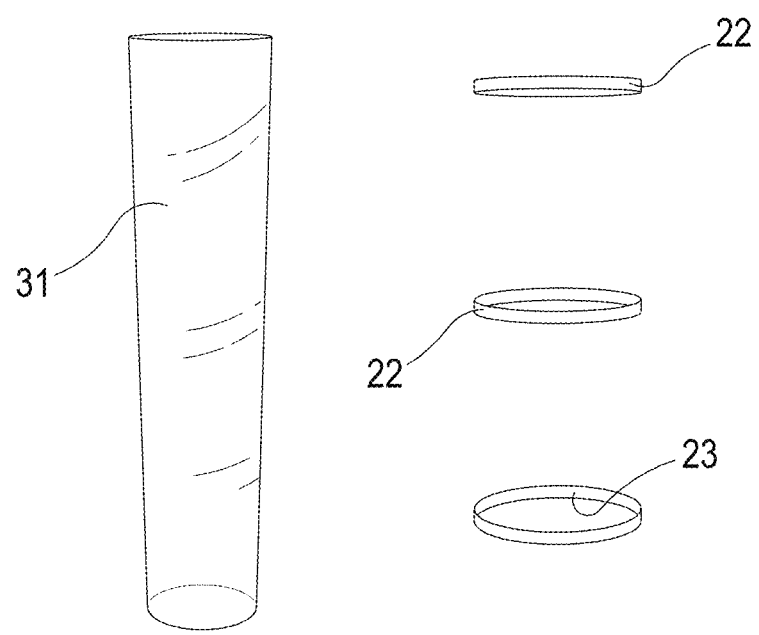

In FIGS. 7 to 12 different constructive variations of a third embodiment are showed, wherein the photocatalytic reactor is built inside a common water filter of which FIG. 7 shows the external view. The water filter comprises an external socket 31 and a net 32 adhering to the inner surface of the socket. The net is treated, i.e. covered with the photocatalyst. A cartridge 33 made of plastic material and covered by nylon fabric with micro-holes of 60 microns is coaxially supported inside the socket. Inside said cartridge the photocatalytic reactor 133 is inserted on a laminar support or yarn support or other structure on a support and forming channels, all of the construction being transparent to light. The illumination with the necessary LEDs will be placed outside depending on the type of hydraulic assembly as depicted in the example of FIGS. 7 and 11 and 12. The strips 22 of LEDs 23 are in the form of annular elements inserted on the external wall of the socket and distributed along the axial extension thereof, with the LED sources 23 facing the inside of the socket relative to the emission direction. Other alternatives can also be provided, possibly in combination to each other as arrangements of the rectilinear strips oriented parallel to the axis of the socket and/or one or more helical strips that wind on the outer surface of the socket.

A header 38 locks said concentric tubes, containing at least two openings, at least one for the inlet 39 of the fluid to be sanitized, at least one for the outlet 40 of the sanitized fluid. The fluid enters through the inlet 39, crosses all of the set of parts described and adheres first to the net and then crosses the micro-holes of the coating of the cartridge and, finally, adheres to the photocatalytic reactor inside the cartridge itself. Thus the sanitized liquid exits at 40. The strips 22 of LED lights 23 are placed outside the tube according to the construction.

Further features and advantages of the object of the present invention will be better highlighted by specific examples having the function of better clarifying the invention, which examples must not be considered as a limitation to the invention itself.

EXAMPLE 1

Photocatalytic antibacterial reactor for ambulances or goods transport vehicles not under the ATP regimen that can be used where an air conditioner using a cold or hot/cold evaporator exists.

The reactor works constantly with the evaporator running (does not require operation with the vehicle stationary or in the absence of personnel on board, as other instruments).

The photocatalytic reactor used is that described in FIG. 1.

Number of sheets made of zirconated steel:
Sheet size: 400×35×0.8 mm
Distance between the sheets: 7.5 mm/15 mm
Power supply: 12/24 Vcc
Power consumption: 12-14 W mt
Color temperature: 6000-65000 K
Light flow: 1200 Lm/mt
LED number per channel: 2
Beam angle: 120°
Turn-on time <0.3 sec
Vehicle: New Renault Trafic Loading compartment: 5 $m^3$ with cover in HCCP regimen Test Process
1) A container containing sterile water has been placed in the loading compartment of the vehicle causing bubbling by way of vacuum (connecting it to a specific external equipment) such to aspirate the bacterial load in the compartment;
2) The inner environment of the loading compartment, when the vehicle is stationary and the system is deactivated, has been conveniently contaminated by vaporizing polluted water in the same and letting it bubble for 30 minutes, at the end of which the sterile container has been collected and the water contained therein has been analyzed in order to verify the bacterial load at the beginning of the activity and as such initial element of the analysis;

the AC system equipped with filter has been switched on and run for 30 minutes, after which it has been switched off by inserting again the container with sterile water (in the meantime sterilized for 30 minutes in oven) by aspirating and bubbling environmental air for 30 minutes, after which the sample was collected and the water contained therein has been analyzed with the same methodology of the previous point, thus representing T1 of the analysis.

3) The same type of analysis of the previous point has been repeated with additional 30 minutes of operation of the system, making overall a total of 1 h of treatment and the analysis datum thus obtained represented the datum highlighted with T2 in the analysis.

4) The machine has been left off and closed overnight and the following morning the analysis has been repeated (still with the same parameters) after 1 h of continuous operation of the system, making overall a total of 2 h of treatment. The datum so detected represents the T3 value of the analysis.

The investigation has been made (ref. Method UNI EN ISO 13098:2002 regulations) on:

TOTAL BACTERIAL LOAD AT 37° C.
TOTAL BACTERIAL LOAD AT 22° C.
STREPTOCOCCI
MOLDS AND YEASTS

Results obtained (see Table 1):

following the checks made, in the first 30 minutes it has been approximately obtained an abatement around 99% of the searched parameters (TBL at 22° and at 37° C.—Fungi and Streptococci)

in the second minutes a further abatement around 20-50% of the remaining pollution;

after the following hour (2 hours of treatment in total) started after the night break at rest, the abatement was total as we haven't found anymore any of the bacteria searched.

TABLE 1

| BACTERIOLOGICAL PARAMETERS | Before T0 | After 30' T1 | After 60' T2 | After 120' T3 |
|---|---|---|---|---|
| Total bacterial load at 22° C. | 30,303 | 380 | 185 | N.D. |
| Total bacterial load at 22° C. | 18,939 | 190 | 111 | N.D. |
| Molds and yeasts | 22,727 | 190 | 140 | N.D. |
| Fecal streptococci | 15,050 | 120 | 100 | N.D. |

(Ufc/m³)

EXAMPLE 2

The analysis has been carried out by using Petri capsules of non-selective agarized medium (PDA, Potato dextrose agar) place inside the laminar flow suction hood Asalair 1200 before and after treatment of the air by means of the photocatalytic reactor described in FIG. 1. The initially sterile environment used for the treatment with the photocatalytic reactor has been placed in contact with the external air, by deactivating the UV light and the laminar air flow, thus allowing to lose the sterility. This operation has been performed for 30 minutes. The Petri capsules containing PDA medium have been placed inside the suction hood, isolating the inner environment from the external one and so impeding the air exchange. The cover of the Petri capsules has been removed, allowing the bacterial and fungal load contained in the air to contact the agarized medium and they have been kept inside the suction hood for 30 minutes. Subsequently, the Petri capsules have been incubated at 23° C. in the dark for 10 days inside the incubator. After the removal of the Petri capsules from the environment used for the analysis, the photocatalytic reactor has been placed inside the suction hood and left running for 30 minutes. Subsequently some cleaned Petri capsules have been placed again with PDA medium and the previous steps have been repeated. After the incubation, the analysis of the bacterial and fungal colonies that formed on the plates with agarized medium has been performed.

Hereinafter (in Table 2a and 2b) the results of the analyses carried out before and after the treatment with the photocatalytic reactor are reported TABLE 2 a

| Plate n. | Bacterial colonies without treatment | Bacterial colonies after treatment | Fungal colonies without treatment | Fungal colonies after treatment |
|---|---|---|---|---|
| 1 | 1 | — | 1 | — |
| 2 | — | 1 | 1 | — |
| 3 | — | — | 4 | — |
| 4 | — | — | 2 | — |
| 5 | — | — | 1 | 2 |
| 6 | — | — | 2 | 2 |

TABLE 2 b

| Analysis | Bacterial colonies average | Fungal colonies average | Bacterial colonies standard deviation | Fungal colonies standard deviation |
|---|---|---|---|---|
| Without treatment | 0.17 | 1.84 | 0.41 | 1.17 |
| After treatment | 0.17 | 0.67 | 0.41 | 1.03 |

By analyzing the results obtained, it highlighted a significant difference between fungal load isolated before the treatment with the photocatalytic reactor and that after the treatment. Only 2 plates on a total of 6 have fungal colonies after using the photocatalytic reactor and both have 2 different species. In the tests carried out before the treatment, the variability of species is much higher and mostly species of Ascomycetes such as *Penicillium* and *Aspergillus*, but also *Cladosporium* and hyaline colonies have been detected. Thus, the activity of treating the air proved to be effective, removing much of the fungal load contained therein, in particular the most significant activity is on the *Aspergillus* and *Penicillium* species that are completely abated, whereas there is the causal appearance of other species such as *Apiospora montagnei* and *Acremonium*. No difference emerged for what concerns the treatment of the bacterial load, which remains low in both tests performed.

The abatement of the fungal load of species such as *Aspergillus* or *Penicillium* is very important because they are not only the main responsible for the pollution with bacterial and fungal cultures of interest for the research in many environments, but they are also a cause for problems at the level of human health, causing serious respiratory problems in immunocompromised individuals.

EXAMPLE 3

Extractor/fan integral with a photocatalytic reactor same as that described in FIG. 2 for sanitizing the air in transit through the system, in one passage only.
1) In the room identified as reference environment for performing the test, the equipment undergoing the check has been placed.

In order to facilitate the verification of the functioning of the system, the outlet of the extractor has been catalyzed and suitably prepared so as to allow the extraction of the air stream treated by the photocatalytic system. The collection has been made with an instrument called "Bio Sampler" consisting of a test tube containing sterile water in which the air aspirated to be tested has been bubbled, by means of a specific external pump so as to transfer the bacterial load in the air to the sterile liquid contained in the test tube.

2) 3 sampling of the duration of 15 minutes each have been performed.
   a) The first of these has been the sampling of the air in the test environment to test the basal bacterial load used for checking the possible abatement in the following tests; thus the environmental collection has in no way been subject to sanitizing treatment.
   b) The second sampling has been made by collecting the air exiting the extractor with the fan at the minimum speed.
   c) The third sampling has been made by collecting the air exiting the extractor with the fan at the maximum speed.

The investigation has been made (ref. Method UNI EN ISO 13098:2002 regulations) searching for the following reference bacteriological indicators:
TOTAL BACTERIAL LOAD AT 37° C.
TOTAL BACTERIAL LOAD AT 22° C.
MOLDS AND YEASTS Results obtained (see Table 3):
after the checks that have been done, an abatement differentiated not only for what concerns the different air speed crossing the system but also based on the type of the bacteria searched (TBL at 22° and at 37° C.—molds and yeasts) has been obtained
in the first test the abatement obtained has settled around 66% for TBL, whereas the total abatement of the remaining pollution has been obtained.
in the second test the abatement obtained has been even more differentiated as an abatement around 33% on BCT at 22° C. has been obtained, whereas the one at 37° C. has been abated by 80%; on the other hand, the abatement for the yeasts and molds has been equal to 100% in total.

TABLE 3

| BACTERIOLOGICAL PARAMETERS | (Ufc/m$^3$) | | |
| --- | --- | --- | --- |
| | POLLUTED ENVIRONMENTAL AIR Test 0 | MIN SPEED Test 1 | MAX SPEED Test 2 |
| Total bacterial load at 22° C. | 15 | 5 (−66%) | 10 (−33%) |
| Total bacterial load at 22° C. | 25 | <1 (−100%) | 5 (−80%) |
| Molds and yeasts | 5 | <1 (−100%) | <1 (−100%) |

In the light of the results achieved, it is evident that the photocatalytic reactor used for sanitizing the air in one passage only works, although in a differentiated way, based on the type of bacteria and throughput in the treatment system.

EXAMPLE 4

Extractor/fan integral with a photocatalytic reactor for sanitizing the air in transit through the system, in one passage only or with recirculation in a rest room in use at a craft workshop.
1) In the room identified as reference environment for performing the test, the equipment undergoing the check has been placed.

In order to facilitate the verification of the functioning of the system, the outlet of the extractor has been catalyzed and suitably prepared so as to allow the extraction of the air stream treated by the photocatalytic system. The collection has been made with an instrument called "Bio Sampler" consisting of a test tube containing sterile water in which the air aspirated to be tested has been bubbled, by means of a specific external pump so as to transfer the bacterial load in the air to the sterile liquid contained in the test tube.

2) 3 sampling of the duration of 30 minutes each have been performed.
   a) The first test has been performed by collecting the air in the environment at time zero to check the existing contamination.
   b) The second test has been performed by activating the aspiration of the outside air and subjecting it to one photocatalytic treatment only with a suction hood, for 30 minutes; in this moment the environmental air of the room has been sampled for 30 minutes.
   c) Also the third test has been performed with the same operative mode, 30 minutes restoring the initial conditions, then 30 minutes recirculation with 2 suction hoods and finally the collection of environmental air for 30 minutes.

The investigation has been made (ref. Method UNI EN ISO 13098:2002 regulations) searching for the following reference bacteriological indicators:
TOTAL BACTERIAL LOAD AT 37° C.
TOTAL BACTERIAL LOAD AT 22° C.
MOLDS AND YEASTS Results obtained (see Table 4):
As it can be noted from the results obtained, the bacteriological part has been zeroed, even after one passage only, by the photocatalytic system and, even if the contaminant values at time zero are very low, this does not cancel the result obtained.

TABLE 4

| BACTERIOLOGICAL PARAMETERS | TIME ZERO Test 1 | ONLY ONE PASS AND 1 SUCTION HOOD Test 2 | RECIRCULATION WITH 2 SUCTION HOODS Test 3 |
|---|---|---|---|
| | (Ufc/m³) | | |
| Total bacterial load at 22° C. | 0 | 0 | 0 |
| Total bacterial load at 22° C. | 10 | 0 | 0 |
| Molds and yeasts | 10 | 0 | 0 |

FIG. 13 shows an embodiment of the filtering unit according to an embodiment of the present invention. The filtering unit comprises a tubular container 140 closed at one end thereof, coaxially housing a cylindrical filtering cartridge 141 inside it.

The filtering cartridge 141 has a mantle wall constituted by a grid or a porous material having size of the meshes or pores of the type usually used for example for the water filtration or the like. The cartridge is closed at one head end that is on a side thereof corresponding to the closed end of the container 140. Both the filtering cartridge 141 and the container 140 are open at the opposite end and this end is linked to an inlet union 142 and an outlet union 143, respectively.

As it is evident, the mantle wall shaped as a grid of the cartridge can be stiffened by a combination of axial and circumferential ribs on which the grid-like wall rests.

Both the wall of the container 140 and the wall of the cartridge have transmissibility to the light radiation activating a photocatalyst.

The photocatalyst material is applied on a supporting element, not visible in FIG. 13, that is made as depicted in FIG. 15 and is denoted by 150. This supporting element of the photocatalyst material is constituted by a plurality of axial fins 151 radially oriented and arranged so as to form a crown along a circumference. The outer diameter of the crown of radial fins 151 is smaller than the inner diameter of the cylindrical filtering cartridge 141.

The radial fins 151, in pairs of diametrically opposite fins, are coincident with a diametrical plane of said element 150.

The fins are kept in position at their ends by rings 152.

According to a further feature that can be provided alternatively or in combination with the supporting element 151, the photocatalytic material is provided on the mantle wall and/or reinforcing ribs of the filtering cartridge 141.

The illumination source emitting the light radiation activating the photocatalyst is constituted by a band made of flexible material 144 on which the LED strips 145, that are oriented parallel to the winding axis of said band around the mantle wall of the container 140, are fixed with predetermined distances to each other.

The extent of said band perpendicularly to the longitudinal extent of the LED strips 145 is substantially equal to that of the development on the plane of the mantle wall of the container 140, i.e. the maximum diameter thereof, if the shape of said container is slightly a truncated cone.

According to a possible feature, the arrangement of the LED strips on the band 144 made of flexible material is such that the LED strips are placed in intermediates points of the succession of adjacent radial fins, by orientating the beam emitted in the angular region generated by the same and by illuminating the facing surfaces of the adjacent fins of the column of fins 151.

The band can be formed by two layers coupled to each other and covering the sides of the LED strips to which the conductors for the power supply are connected, thus a common power supply wire 146 branching to the various LED strips 145 inside the pocket formed by at least two layers coupled to each other of the flexible band being exited sealingly from said band.

Still according to a feature, the inner surface of the band made of flexible material 144 is made of, or coated by, a layer of reflective material whose reflectivity parameters are optimized on the wavelengths of the light radiation activating the photocatalytic material.

As it is evident, the band 144 is wound around the container 140, whereas on a terminal edge parallel to the axis of the container, means fixing to the corresponding opposite edge of said band 144, allowing to tighten the band in position on the container 140, are provided.

An embodiment provides that said fixing means are made of a material of the Velcro® type, one of the ribbons being placed along a first edge 146 of two edges of the band parallel to the axis of the container 140 and/or LED strips 145, on the external surface of the band 144, whereas the other ribbon is provided on an extension of the opposite edge 147 of the band 144 intended to overlap with the ribbon on said first edge.

Still according to a further feature, both the filtering cartridge 141 and the supporting element 150 of the photocatalytic material are made modular, a module being provided with a minimum axial length of both of these elements 141 and 150, which length is defined correspondingly and such that it is possible to generate filtering cartridges 141 and corresponding supporting elements 150 of the photocatalytic material having length equal to multiples of said minimum length by axially aligning to each other the individual modules having minimum length.

These can be removably fixed to their ends facing head-to-head thanks to any type of fixing member, such as for example screws, bolts, rivets, interlocking means, ring nuts locking the ends of the modules facing to each other and/or also by gluing or welding.

In FIGS. 13 and 15 an embodiment is shown wherein both the filtering cartridge 141 and the supporting element of the photocatalytic material 150 are constituted respectively by two modules coupled to each other and having minimum length.

A further feature can provide that also the band 144 with the LED strips 145 has a length corresponding to said minimum length and that, in case of combination of several modules, the individual bands 144 are mounted one after the other along the longitudinal extent of the set of modules.

In the example of FIGS. 13 to 15, the choice has been made by providing a band whose minimum length is corresponding to the length of two modules of filtering cartridge 141 and/or supporting element of the photocatalytic material 150.

FIG. 15 shows an embodiment variation of the filtering unit according to FIG. 13, that differentiates because the inlet and the outlet of the filter are not provided on the same end of the container. The latter his has been made in the form of tubular element that is inserted thanks to the nuts of the ends in a feeding pipe of a fluid flow. The construction of the cartridge 141 and supporting element of the photocatalytic material, as well as the construction of the band 144 bearing the LED strips 145, are essentially identical to those described with reference to the previous example.

As it is evident from FIG. 15, the embodiments depicted have the advantage that the support 150 for the photocatalytic material and the illumination source can be made as integration kit for existing filtering structures. In general, such existing filtering unit have standardized sizing, therefore by defining accordingly the diameters of the supporting element 150 of the photocatalytic material and the minimum length of the module when a modular construction is provided, and the size of the band 144 in axial direction and in circumferential direction, it is possible to produce universal kits that adapt to the different configurations of existing filtering units.

Furthermore as it is evident, the particular implementation of the illumination source in the form of band outside the container of the flow releases the installation of the hydraulic part from the electric one and simplifies the construction and maintenance activities that can thus be given, depending on the type of work, to a plumber or an electrician.

FIGS. 16 to 21 show different constructive variations of a device according to the present invention that is particularly suitable for the treatment of gaseous fluid flows, such as for example fumes and/or air.

In FIG. 16 a framework 160 supports two orders, i.e. two layers 161 and 162 of sheets 163 and 164 respectively side by side. The extent of the framework 160 is equal to at least twice the width of the sheets 163. On the surfaces of the sheets 163 the photocatalytic material is provided. The sheets 163 are parallel to each other and perpendicular to the sheets 164 that are also parallel to each other thus forming a grid that is intended to be placed perpendicularly to the axis of a duct through which the gaseous fluid is passing or on a delivery mouth of said gaseous fluid into an environment.

Each array 161, 162 of sheets provides, in median position, i.e. coincident with a central plane perpendicular to the sheets themselves, an illumination source 165, 166 that is made in the form of at least one rectilinear LED strip.

According to a feature, the LED strip has one LED for each channel delimited by two adjacent sheets, 163 and 164 respectively. Preferably each strip has two LEDs for each of said channels, which LEDs are oriented to emit the radiation beam in opposing directions, thus illuminating a corresponding half of said channel.

Also in this case, the device can constitute a base module as it is possible to place two or more of said devices side by side in the direction of the fluid flow.

Furthermore, since in general the sections of the channels and/or delivery mouths are of standard size, it is possible to implement the device of FIG. 16 with a frame adapted to said standard size and that can be installed in retrofitting operations of existing systems.

FIG. 17 shows an embodiment variation providing only one array 161 of sheets and a corresponding illumination source with one LED for each channel delimited by the sheets 163. In this case this unit can be used in an environment with a reduced volume such as cold rooms, refrigerators, loading compartments, ambulances and other closed spaces or spaces that can be closed.

FIG. 18 shows a variation of the example of FIG. 16 wherein different sizes are provided.

FIGS. 19 to 21 show a device according to the present invention, configured to cooperate with console of conditioning systems and that potentially may be provided as additional accessory that can be installed also in a second moment with respect to the console and thus also suitable to retrofitting operations.

As it is shown in the figures, the device comprises a frame 200 as a basin with a cross section like a rectangular trapezium reversed upside down and with the major base oriented upwards and open.

In the frame 200 next to at least one, preferably two or more or all of the delivery mouths, groups 201 of fins 202 parallel to each other and having a section corresponding to the cross-section of the frame, and thus a trapezoidal plan shape, are provided. On the perpendicular wall there is at least one line of LEDs, possibly also several lines of LEDs mounted on a common support and constituting the illumination source 203, the LEDs being distributed so that at least one LED 204 is coincident with a channel formed by two adjacent fins 202.

The fins constitute the supporting elements for the photocatalytic material and the conveyors of the fluid flow in the channels delimited by the same and in which the reaction with the photocatalyst occurs.

The wall perpendicular to the two bases of the rectangular trapezium section of the frame 200 constitutes the back or bottom wall of the frame, whereas the outlet of the sanitized flow is on the opposite side of the frame 200.

FIG. 21 shows an example of installation. By 210 it is schematically depicted a wall console of a conditioner. The air flow F emitted by the lower delivery mouth 211 is intercepted by the device according to FIGS. 19 and 20 that is mounted directly to the same wall or the same bearing structure of the console 210 and in FIG. 21 is globally denoted by 213.

As it is evident, the device is mounted at the bottom of the console, i.e. the outlet emitting the flow F and the particular profile of the frame 200 causes the emitted air to pass in the channels between the sheets and thus to be treated by the photocatalyst and thus to be conveyed again into the environment from the front wall slightly tilted upwards.

The basin-like shape generates a vortex with axis parallel to the longitudinal extent of the frame 200 and the longitudinal extent of the outlet mouth of the console 210 and thus maximizes the permanence of the flow emitted by the conveyor in the reaction region before returning to the environment.

Therefore, object of the invention is also a sanitizing device by means of photocatalyst that is made as an accessory separated from a console of a conditioner and that can be mounted at the outlet emitting the air flow of said console.

According to a variation, it is also possible to provide fixing elements to fix the device 210 directly to the frame and/or case of the console of the conditioner.

For what concerns the type of photocatalysts, the embodiments described of the device according to the invention can be provided in combination with any photocatalyst.

However, the best results in terms of efficiency and effectiveness are obtained by combining the constructions described above with the preferred photocatalyst defined above.

The above also applies to the features of intensity and/or wavelength and/or color of the activating light radiation and/or to the preferred materials used for the supports of the photocatalyst material.

The invention claimed is:

1. A sanitizing photocatalytic reactor suitable for gaseous or liquid fluids, comprising:
   a reaction region containing a photocatalyst that is a photocatalytic material activated with sunlight, the photocatalyst being distributed on one or more supports made of an inert material or mixed with a matrix made from a plastic material; and an illumination source oriented so as to emit light radiation beams incident on said photocatalyst distributed on said support, the illumination source being constituted by one or more white color LED lights;

wherein said reaction region comprises one or more channels through which said fluids to be sanitized flow, said one or more channels being delimited and/or containing said one or more supports for the photocatalyst, wherein the sanitizing photocatalytic reactor is shaped as tubular element having a tubular segment, through which a liquid fluid is passing, and inside which the one or more supports for the photocatalyst are provided, the illumination source being provided internally or externally to said tubular element, the tubular element being transparent at least when the illumination source is arranged externally to the tubular element, wherein the tubular segment comprises two coaxial tubes of different diameters arranged one inside the other so as to form a channel through which a fluid flow is passing, the channel having an annular section being delimited by the tube having a smaller diameter and by the tube having a larger diameter, the tube having the larger diameter being made of the inert material partially or completely covered on an inner surface of the tube by a layer of the photocatalytic material activated by light radiation with a spectrum corresponding to sunlight, the tube having the smaller diameter being made of a material transparent to the light radiation that actives the photocatalyst, the tube having the smaller diameter housing in its inside at least one strip of LED lamps placed parallel to a longitudinal extent of the tube having the smaller diameter and adjacent to or on an inner or outer surface of said tube having the smaller diameter, wherein the sanitizing photocatalytic reactor is provided in combination with a filtering unit of a liquid fluid, the filtering unit comprising a tubular container, inside which a tubular cylindrical filtering cartridge is provided that comprises mantle walls constituted by a grid, an inner surface of said grid being covered by synthetic fabric with micro-holes, said grid and said synthetic fabric providing supporting surfaces for the photocatalyst, wherein inside said filtering cartridge a supporting element is housed for the photocatalyst, the supporting element being coaxial to said filtering cartridge, wherein one end of said filtering cartridge is closed and another end of said filtering cartridge is linked to a fluid inlet union, wherein the tubular container is closed at one end and is linked to an outlet union at an opposite end, and wherein one or more illumination sources are provided that comprise a set of LED lamps that radiate an activating light radiation on surfaces, provided with the photocatalyst of the filtering cartridge, of the support for the photocatalyst provided inside the filtering cartridge and of a layer of the synthetic fabric which covers internally said grid.

2. The sanitizing photocatalytic reactor according to claim 1, wherein said one or more supports are made from a material having a low transmission coefficient or zero transmission coefficient for the light radiation incident on the photocatalyst.

3. The sanitizing photocatalytic reactor according to claim 1, wherein the photocatalyst is deposited on a surface or surfaces exposed to the light radiation activating the photocatalyst and/or impregnated in a matrix of a material from said supports, in the form of particles having a nanometric size that ranges between 1 and 100 nm.

4. The sanitizing photocatalytic reactor according to claim 1, wherein one or more supports for the photocatalyst constitute a constructive unit independent of constructive elements constituting the illumination source and hardware or software units supplying power to the illumination source, said constructive elements being provided with mutual fixing removable elements.

5. The sanitizing photocatalytic reactor according to claim 1, wherein the photocatalyst comprises $WO_3$.

6. The sanitizing photocatalytic reactor according to claim 1, wherein said light radiation has an intensity of at least 300 Lux, and a white color ranging from 5300° K to 10000° K.

7. The sanitizing photocatalytic reactor according to claim 1, wherein the light radiation is emitted with a propagation direction incident on surfaces of the one or more supports of the photocatalyst and with an opening angle ranging from 100 to 120°.

8. A sanitizing photocatalytic reactor suitable for air liquid or liquid fluids, comprising:

a reaction region containing a plurality of sheets of an inert support, the sheets being placed parallel to one another and equally spaced at a minimum distance from one another of 7.5 mm, thus forming several substantially uniform channels, said sheets being covered by a layer of photocatalytic material structured to be activated by solar light radiation and/or by a light radiation generated by a lighting lamp emitting a white color light; and a supporting region of an illumination source with LED lights emitting a white color light radiation with an opening and a propagation direction of a beam incident against walls of said sheets so as to illuminate said sheets, said illumination source being constituted by at least one LED lamp for each channel laterally delimited by two adjacent sheets, said at least one LED lamp being distributed along the illumination source in such a position so as to coincide with a corresponding channel, wherein the plurality of sheets comprises at least one first layer of sheets parallel to each other and having sides oriented in a direction of fluid flow and at least one second layer of sheets parallel to each other and having sides oriented in the direction of the fluid flow, the sheets of the first layer having longitudinal axes oriented in anon-parallel direction to longitudinal axes of the sheets in the second layer of sheets, and wherein, for the first layer of sheets and the second layer of sheets, a dedicated illumination source is provided that comprises at least one line or strip of LED lamps, which is oriented in a direction perpendicular to the longitudinal axes of the sheets of the first and the second layer of sheets, said illumination source contributing to an activation of the photocatalytic material.

9. The sanitizing photocatalytic reactor according to claim 8, wherein said illumination source comprises one or more strips of LED lamps and is supported by one or more of said sheets, said one or more strips of LED lamps being optionally mounted on a container within which a power supply of said one or more strips of LED lamps is placed, the container being perpendicular to parallel axes of the sheets, and further being in contact with or near said parallel sheets.

10. The sanitizing photocatalytic reactor according to claim 8, wherein the sanitizing photocatalytic reactor is configured as an accessory mountable inside distribution channels of a fluid flow and/or at a delivery and/or a suction mouth of said fluid flow and is made as a unit separated from said distribution channels, delivery, or suction mouth and is further configured to be removably fixed to or in the distribution channels, delivery, or suction mouth.

11. The sanitizing photocatalytic reactor according to claim 1, wherein a wall of the tubular segment having the larger diameter and the tubular container of the filtering cartridge are made of a transparent material having transmissivity of the light radiation activating the photocatalyst, and wherein the one or more illumination sources are provided outside a mantle wall of said tubular segment or said tubular container and are oriented so as to emit a beam of the light radiation towards an inside of said tubular segment or said tubular container, a power supply unit of said one or more illumination sources being provided outside said tubular segment or said tubular container.

12. The sanitizing photocatalytic reactor according to claim 11, wherein the one or more illumination sources are configured to be fixed separately from said tubular segment or said tubular container.

13. The sanitizing photocatalytic reactor according to claim 11, wherein the one or more illumination sources are selected from one or a combination of the following variations:
- annular supporting elements of a plurality of LED lamps provided on a radially inner side of the said annular supporting elements, one or more of said annular supporting elements being adapted to be fixed in predetermined axial positions according to predetermined distributions along an axial extent of the tubular segment or the tubular container;
- LED lamps mounted in a line on one or more strips on a flexible, ribbon-shaped support configured to be helically wound around the mantle wall of the tubular segment or the tubular container; and
- one or more strips of adjacent LED lamps mounted at predetermined distances on a band made of a flexible material, the band being adapted to be wound around the mantle wall of the tubular segment or the tubular container, the one or more strips of adjacent LED lamps being oriented parallel to a winding axis of the tubular segment or the tubular container.

14. The sanitizing photocatalytic reactor according to claim 13, wherein an inner wall of said band is made of a reflective material for the activating radiation emitted by the LED lamps.

15. The sanitizing photocatalytic reactor according to claim 14, wherein, inside the tube segment and/or the filtering cartridge, a support made of an inert material for the photocatalytic material is housed, said support being constituted by a plurality of sheets arranged to have longitudinal axes parallel to each other and crossing each other at median longitudinal axes, and wherein the one or more illumination sources have at least one LED lamp or at least one line of LED lamps placed coincident with a corner region delimited by two adjacent sheets.

16. The sanitizing photocatalytic reactor according to claim 14, wherein the tubular segment and/or the tubular container have different lengths that are equal to a predetermined multiple of a minimum length, the supporting element finned for the photocatalytic material and the filtering cartridge respectively being constituted by at least one module or by an axial combination of a plurality of modules each constituted by an axial segment of a supporting element and said filtering cartridge respectively having a length corresponding to the said minimum length of the tubular segment or the tubular container, said plurality of modules being adapted to be fixed to each other in axially aligned position and, optionally, the one or more illumination sources having a modular construction comprising a module having a minimum axial length on which lines of LED lamps having a corresponding minimum axial length are distributed, said minimum axial length being commensurate with an axial length of the modules of the supporting element and the modules of the filtering cartridge.

17. The sanitizing photocatalytic reactor of claim 16, wherein the LED lights have:
- a power supply of 12 to 24 Vcc,
- a power consumption of 12 to 14 W mt,
- a color temperature of 5300° K to 10000° K corresponding to cold white,
- a light flow of 1100 to 1600 Lm/mt,
- a beam angle from 100 to 120°, and
- a turn-on time lower than 0.3 sec.

18. The sanitizing photocatalytic reactor according to claim 17, wherein said sanitizing photocatalytic reactor is configured as a treatment accessory adapted to be coupled to a console of a conditioner device, said treatment accessory being configured as a basin adapted to be mounted downstream of an output opening of an air flow from said console of the conditioner device and comprises a plurality of sheets oriented in a direction of said air flow emitted by said console, said plurality of sheets being side by side and parallel to each other and at a predetermined distance, said plurality of sheets supporting the photocatalytic material, further comprising an illumination source of surfaces of said plurality of sheets which comprises at least one LED lamp for each channel delimited by adjacent sheets and oriented in a flow direction of a fluid between said sheets.

19. A combination of a conditioner console and an accessory comprising a treatment reactor according to claim 1.

* * * * *